(12) United States Patent
Weinstein et al.

(10) Patent No.: US 6,569,638 B1
(45) Date of Patent: May 27, 2003

(54) METHOD FOR SCREENING COMPOUNDS FOR THE TREATMENT OF NEOPLASIA

(75) Inventors: I. Bernard Weinstein, Englewood, NJ (US); W. Joseph Thompson, Doylestown, PA (US); Jae-Won Soh, Cliffside Park, NJ (US); Li Liu, Ambler, PA (US); Han Li, Yardley, PA (US)

(73) Assignee: Cell Pathways, Inc, Horsham, PA (US)

( * ) Notice: Subject to any disclaimer, the term of this patent is extended or adjusted under 35 U.S.C. 154(b) by 0 days.

(21) Appl. No.: 09/517,734

(22) Filed: Mar. 3, 2000

(51) Int. Cl.$^7$ ................................................. C12Q 1/48

(52) U.S. Cl. ........................ 435/15; 435/69.2; 435/184

(58) Field of Search .......................... 435/15, 69.2, 184

(56) References Cited

U.S. PATENT DOCUMENTS

| | | |
|---|---|---|
| 3,031,450 A | 4/1962 | Fischer et al. |
| 3,161,654 A | 12/1964 | Shen |
| 3,322,755 A | 5/1967 | Roch et al. |
| 3,517,005 A | 6/1970 | Cronin et al. |
| 3,594,480 A | 7/1971 | Cronin et al. |
| 3,647,858 A | 3/1972 | Hinkley et al. |
| 3,654,349 A | 4/1972 | Shen et al. |
| 3,780,040 A | 12/1973 | Schnettler et al. |
| 3,812,127 A | 5/1974 | Cronin et al. |
| 3,819,631 A | 6/1974 | Broughton et al. |
| 3,865,840 A | 2/1975 | Carson |
| 3,920,636 A | 11/1975 | Takahasi et al. |
| 4,001,237 A | 1/1977 | Partyka et al. |
| 4,001,238 A | 1/1977 | Partyka et al. |
| 4,039,544 A | 8/1977 | Broughton et al. |
| 4,060,615 A | 11/1977 | Matier et al. |
| 4,076,711 A | 2/1978 | Ganguly et al. |
| 4,079,057 A | 3/1978 | Juby et al. |
| 4,098,788 A | 7/1978 | Crenshaw et al. |
| 4,101,548 A | 7/1978 | Crenshaw et al. |
| 4,102,885 A | 7/1978 | Crenshaw et al. |
| 4,138,561 A | 2/1979 | Crenshaw et al. |
| 4,146,718 A | 3/1979 | Jenks et al. |
| 4,161,595 A | 7/1979 | Kaplan et al. |
| 4,171,363 A | 10/1979 | Crenshaw et al. |
| 4,208,521 A | 6/1980 | Crenshaw et al. |
| 4,209,623 A | 6/1980 | Juby |
| 4,423,075 A | 12/1983 | Dvornik et al. |
| 4,457,927 A | 7/1984 | Biere et al. |
| 4,460,590 A | 7/1984 | Möller |
| 4,460,591 A | 7/1984 | DeGraw et al. |
| 4,837,239 A | 6/1989 | Benjamin et al. |
| 4,880,810 A | 11/1989 | Lowe III et al. |
| 4,885,301 A | 12/1989 | Coates |
| 4,923,874 A | 5/1990 | McMahon et al. |
| 4,971,972 A | 11/1990 | Doll et al. |
| 5,073,559 A | 12/1991 | Coates |
| 5,091,431 A | 2/1992 | Tulshian et al. |
| 5,147,875 A | 9/1992 | Coates et al. |
| 5,175,151 A | 12/1992 | Afonso et al. |
| 5,223,501 A | 6/1993 | Chakravarty et al. |
| 5,239,083 A | 8/1993 | Kumazawa et al. |
| 5,250,535 A | 10/1993 | Verheyden et al. |
| 5,254,571 A | 10/1993 | Coates et al. |
| 5,358,952 A | 10/1994 | Moschel et al. |
| 5,376,683 A | 12/1994 | Klar et al. |
| 5,393,755 A | 2/1995 | Neustadt et al. |
| 5,401,774 A | 3/1995 | Pamukcu et al. |
| 5,439,895 A | 8/1995 | Lee et al. |
| 5,464,861 A | 11/1995 | Dobrusin et al. |
| 5,488,055 A | 1/1996 | Kumar et al. |
| 5,614,530 A | 3/1997 | Kumar et al. |
| 5,614,627 A | 3/1997 | Takase et al. |
| 5,674,876 A | 10/1997 | Gilbert et al. |
| 5,696,159 A | 12/1997 | Gross et al. |
| 5,728,563 A | 3/1998 | Tanaka et al. |
| 5,731,167 A | 3/1998 | Stracke et al. |
| 5,756,818 A | 5/1998 | Buchmann et al. |
| 5,798,246 A | 8/1998 | Au-Young et al. |
| 5,798,373 A | 8/1998 | Warrellow |
| 5,849,770 A | 12/1998 | Head et al. |
| 5,852,035 A | 12/1998 | Pamukcu et al. |
| 5,858,694 A * | 1/1999 | Piazza et al. .................. 435/19 |
| 5,869,519 A | 2/1999 | Karanewsky et al. |
| 5,874,440 A | 2/1999 | Pamukcu et al. |
| 5,891,896 A | 4/1999 | Warrellow et al. |
| 5,922,595 A | 7/1999 | Fisher et al. |
| 5,932,423 A | 8/1999 | Au-Young et al. |
| 5,932,465 A | 8/1999 | Loughney |
| 5,942,520 A | 8/1999 | Pamukcu et al. |
| 5,948,779 A | 9/1999 | Sperl et al. |
| 6,130,053 A * | 10/2000 | Thompson et al. ........... 435/15 |
| 6,200,771 B1 * | 3/2001 | Liu et al. ...................... 435/19 |

FOREIGN PATENT DOCUMENTS

| | | |
|---|---|---|
| DE | 3038166 | 5/1981 |
| DE | 274218 | 12/1989 |
| EP | 0 330 004 A1 | 6/1989 |

(List continued on next page.)

OTHER PUBLICATIONS

Gajate C. Involvement of c–Jun NH2 Terminal Kinase Activation . . . Molecular Pharmacology 53(4)602–612, 1998.*

Yin L. Molecular Determinants of AHPN Induced Growth Arrest and Apoptosis in Human Lung Cancer Cell Lines. Molecular and Cellular Biology 18(8)4719–4731, 1998.*

(List continued on next page.)

*Primary Examiner*—Ralph Gitomer
(74) *Attorney, Agent, or Firm*—Robert W. Stevenson

(57) ABSTRACT

This invention provides a method to identify compounds potentially useful for the treatment and prevention of neoplasia in mammals. The phosphodiesterase inhibitory activity of a compound is determined along with its ability to elevate JNK kinase activity. Growth inhibitory and apoptosis inducing effects on cultured tumor cells are also determined. Compounds that exhibit phosphodiesterase inhibition, an ability to elevate JNK kinase activity, growth inhibition and apoptosis induction are desirable for the treatment of neoplasia.

8 Claims, 9 Drawing Sheets

FOREIGN PATENT DOCUMENTS

| | | |
|---|---|---|
| EP | 0 347146 A2 | 12/1989 |
| EP | 0 349239 A2 | 1/1990 |
| EP | 0 351058 | 1/1990 |
| EP | 0 352960 A2 | 1/1990 |
| EP | 0 395328 A2 | 10/1990 |
| EP | 0 428268 A2 | 5/1991 |
| EP | 0 463756 A1 | 1/1992 |
| EP | 0 485157 A2 | 5/1992 |
| EP | 0 485158 A2 | 5/1992 |
| EP | 0 485171 A2 | 5/1992 |
| EP | 0 485172 A2 | 5/1992 |
| EP | 0 485173 A2 | 5/1992 |
| EP | 0 508586 A1 | 10/1992 |
| EP | 0 526004 A1 | 2/1993 |
| EP | 0 607439 A1 | 7/1994 |
| EP | 0 743304 A1 | 5/1996 |
| EP | 0 722 937 A1 | 7/1996 |
| GB | 807826 | 1/1959 |
| GB | 2063249 A | 6/1981 |
| JP | 56-53659 A | 5/1981 |
| JP | 57-167974 A | 10/1982 |
| JP | 8-311035 | 11/1996 |
| WO | WO 97/03985 | 2/1967 |
| WO | WO 92/03419 | 3/1992 |
| WO | WO 93/07149 | 4/1993 |
| WO | WO 93/12095 | 6/1993 |
| WO | WO 94/05661 | 3/1994 |
| WO | WO 94/19351 | 9/1994 |
| WO | WO 94/29277 | 12/1994 |
| WO | WO 95 18969 A | 7/1995 |
| WO | WO 95/26743 | 10/1995 |
| WO | WO 97/03070 | 1/1997 |
| WO | WO 97/24334 | 7/1997 |
| WO | WO 98/14448 | 4/1998 |
| WO | WO 98/15530 | 4/1998 |
| WO | WO 98/16224 | 4/1998 |
| WO | WO 98/16521 | 4/1998 |
| WO | WO 98/17668 | 4/1998 |
| WO | WO 98/08848 | 5/1998 |
| WO | WO 98/23597 | 6/1998 |
| WO | WO 98/38168 | 9/1998 |
| WO | WO 96/32379 | 10/1998 |

OTHER PUBLICATIONS

Ahlstrom, M.; Lamberg–Allardt, C., Regulation of adenosine 3',5'–cyclic monophosphate (cAMP) accumulation in UMR–106 osteoblastlike cells: role of cAMP–phosphodiesterase and cAMP efflux, Biochem. Pharmacol. (1999), 58(8), 1335–1340.

Ahn, H.S. et al., Effects of Selective Inhibitors on Cyclic Nucleotide Phosphodiesterases of Rabbit Aorta, Biochemical Pharmacology, vol. 38, No. 19, pp. 3331–3339 (1989).

Ahn, Ho–Sam et al., Potent Tetracyclic Guanine Inhibitors of PDE1 and PDE5 Cyclic Guanosine Monophosphate Phosphodiesterases with Oral Antihypertensive Activity; J. Med. Chem. 1997, 40, pp. 2196–2210.

Altiok N. et al., Bradykinin inhibition of cyclic AMP accumulation in D384 astrocytoma cells. Evidence against a role of cyclic GMP, Neurochem Int. 1992 Sep.; 21(2):209–13.

Anderson, Thomas L. G. et al., Interactions between isoprenaline, sodium nitroprusside, and isozyme–selective phosphodiesterase inhibitors on ADP–induced aggregation and cyclic Nucleotide levels in human platelets (Abstract Only), J. Cardiovasc. Pharmacol. 18(2) pp. 237–242 (1991).

Antonenko S.G. et al., [The role of the components of the cyclic nucleotide system in N–nitrosodiethylamin–induced hepatic carcinogenesis in rats] (Article in Russian), Eksp. Onkol. 1990;12(5):18–21.

Badrieh, Y., et al., Chem. Ber., vol. 125, pp. 667–674 (1992).

Barnett, Mary S. et al., Initial biochemical and functional characterization of cyclic nucleotide phosphodiesterase isozymes in canine colonic smooth muscle (Abstract Only), J. Pharmacol. Exp. Ther., 264(2) pp. 801–812 (1993).

Basu, S. and Kolesnick, R. Stress signals for apoptosis: ceramide and c–Jun kinase. Oncogene, 17: 3277–85, 1998.

Belousova, A. K. et al., Role of cyclic nucleotides in tumor growth regulation, (Article written in Russian) Vestn. Akad. Med, Nauk SSSR (1980), (6), 86–9.

Beltman, Jeryln et al., Characterization of cyclic nucleotide phosphodiesterases with cyclic GMP analogs: topology of the catalytic domains, Mol. Pharmacol. (1995), 47(2), 330–9.

Bergstrand, Hakan et al., Effects of Antiallergic Agents, Compound 48/80, and Some Reference Inhibitors on the Activity of Partially Purified Human Lung Tissue Adenosine Cyclic 3',5'–Monophosphate and Guanosine Cyclic 3',5'-Monophosphate Phosphodiesterase, Molecular Pharmacology, 13, pp. 38–43 (1976).

Biddle, William et al., Antineoplastic Effect of the Pyrimido–Pyrimidine Derivative: RA 233, Pathologie Biologie, Jan., 1984, pp. 9–13.

Bjarnason et al., Gastroenterology, vol. 94, No. 4, pp. 1070–1074 (1988).

Blaya, C. et al., Effect of the protein kinase inhibitors, 1–(5–isoquinolinylsulfonyl)–2–methylpiperazine H–7 and N–(2–[methylamino]ethyl)–isoquinoline–sulfonamide H–8 on Lewis lung carcinoma tumor progression, European Journal of Pharmacology, 354, pp. 99–104 (1998).

Brogden, R.N. et al., Drugs, vol. 16, pp. 97–114 (1978).

Broughton, B.J. et al., Antiallergic Activity of 2–Phenyl–8–azapruin–6–ones, Journal of Medicinal Chemistry, vol. 18, No. 11, pp. 1117–1118 (1975).

Butt, E., Eigenthaler, M., and Genieser, H. G. (Rp)–8–pCPT–cGMPS, a novel cGMP–dependent protein kinase inhibitor. Eur J Pharmacol, 269: 265–8, 1994.

Butt, Elke et al., Characterization of cyclic nucleotide phosphodiesterase with cyclic AMP analogs: topology of the catalytic sites and comparison with other cyclic AMP–binding proteins, Mol. Pharmacol. (1995), 47(2), 340–7.

Cardone, M. H., Salvesen, G. S., Widmann, C., Johnson, G., and Frisch, S. M. The regulation of anoikis: MEKK–1 activation requires cleavage by caspases. Cell, 90: 315–23, 1997.

Carter et al., Chemotherapy of Cancer, $2^{nd}$ Ed., John Wiley & Sons, NY, NY, 1981, pp. 362–365.

Chang, W. et al., Sulindac Sulfone Modulates the Expression and Cellular Localization of b–Catenin in Human Colon Carcinoma Cells, Digestive Disease Week, Apr. 1, 1999.

Chen, Y. R., Wang, W., Kong, A. N., and Tan, T. H. Molecular mechanisms of c–Jun N–terminal kinase–mediated apoptosis induced by anticarcinogenic isothiocyanates. J Biol Chem, 273: 1769–75, 1998.

Chen, Y. R., Wang, X., Templeton, D., Davis, R. J., and Tan, T. H. The role of c–Jun N–terminal kinase (JNK) in apoptosis induced by ultraviolet C and gamma radiation. Duration of JNK activation may determine cell death and proliferation. J Biol Chem, 271: 31929–36, 1996.

Clarke, W. R. et al., The type III phosphodiesterase inhibitor milrinone and type V PDE inhibitor dipyridamole individually and synergistically reduce elevated pulmonary vascular resistance (Abstract Only), Pulm. Pharmacol., 7(2), pp. 81–89, (1994).

Cohan, V. L. et al., In vitro pharmacology of the novel phosphodiesterase type 4 inhibitor, CP–80633, J. Pharmacol. Exp. Ther. (1996), 278(3), 1356–1361.

Cohen L.A. et al., Cyclic nucleotide phosphodiesterase activity in normal and neoplastic rat mammary cells grown in monolayer culture, Cancer Res. 1976 Jun.;36(6):2007–12.

Conti, M. and Jin, S.–L. Catherine, The Molecular Biology of Cyclic Nucleotide Phosphodiesterases, Prog. Nucleic Acid Res. Mol. Biol. 63():1–38, 1999.

Cote, Mylene, et al., Comparative involvement of cyclic nucleotide phosphodiesterases and adenylyl cyclase on adrenocorticotropin–induced increase of cyclic adenosine monophosphate in rat and human glomerulosa cells, Endocrinology (1999), 140(8), 3594–3601.

Curtis–Prior, P.B. et al., Cyclic Nucleotide Phosphodiesterase Activity of Human Normal and Carcinomatous Lung Tissue, The Lancet, pp. 1224–1225 Dec. 4, 1976.

Delporte C. et al., Role of phosphodiesterase II in cross talk between cGMP and cAMP in human neuroblastoma NB–OK–1 cells, Am. J. Physiol. 1996 Jan.;270(1 Pt 1):C286–92.

Dickinson, Natalie T. et al., Activation of cGMP–stimulated phosphodiesterase by nitroprusside limits cAMP accumulation in human platelets: effects on platelet aggregation, Biochem. J. (1997), 323(2), 371–377.

Drees, Markus et al., 3',5'–Cyclic Nucleotide Phosphodiesterase in Tumor Cells as Potential Target for Tumor Growth Inhibition, Cancer Research 53, pp. 3058–3061 (1993).

Duarte, Juan et al., Effects of visnagin on cyclic nucleotide phosphodiesterases and their role in its inhibitory effects on vascular smooth muscle contraction, Gen. Pharmacol. (1998), vol. Date 1999, 32(1), 71–74.

Duggan, D.E. et al., Clin. Pharm. & Therapeutics, vol. 21, No. 3, pp. 326–335 (1976).

Duggan, D.E. et al., J. Pharm. & Exper. Therap., vol. 201, No. 1, pp. 8–13 (1977).

Earnest, D. et al., Piroxicam and Other Cyclooxygenase Inhibitors: Potential for Cancer Chemoprevention, Journal of Cellular Biochemistry, Supplement 161:156–166 (1992).

Easwaran, V. et al., The Ubiquitin–Proteasome Pathway and Serine Kinase Activity Modulate Adenomatous Polyposis Coli Protein–mediated Regulation of β–Catenin–Lymphocyte Enhancer–binding Factor Signaling, The Journal of Biological Chemistry, vol. 274, No. 23, pp. 16641–16645, Jun. 4, 1999.

Eckly–Michel, Anita E. et al., Chelerythrine, a protein kinase C inhibitor, interacts with cyclic nucleotide phosphodiesterases, Eur. J. Pharmacol. (1997), 324(1), 85–88.

Emami S. et al., Histamine and VIP interactions with receptor–cyclic AMP systems in the human gastric cancer cell line HGT–1, Life Sci. 1983 Aug. 1;33(5):415–23.

Epstein, P.M. et al. Increased Cyclic Nucleotide Phosphol Di Esterase Activity Associated with Proliferation and Cancer in Human Murine Lymphoid Cells. Dep. Pharmacol., Univ. Tex. Med. Sch., M.D. Anderson Hospital, Houston, Tex. 77030, USA. BIOSIS: 78:140912 Abstract No Date Avail.

Federation Proceedings (1972) of the Federation of American Societies for Experimental Biology abstract Nos. 2044 and 2045.

Ferreira, S.H. et al., The molecular mechanism of action of peripheral morphone analgesia: stimulation of the cGMP system via nitric oxide release, European Journal of Pharmacology, 201 pp. 121–122 (1991).

Fischmeister, Rodolphe, et al., Cardiac calcium current regulation by the cGMP/NO pathway, C. R. Seances Soc. Biol. Ses Fil. (1996), 190(2–3), 181–206.

Folbergrova J. et al., Cyclic AMP levels of C6 glioma cells treated with cisdichlorodiammine platinum (cis–DDP), Neoplasma 1987;34(1):3–13.

Frattola L. et al., Characteristics of the cyclic AMP–phosphodiesterase activator in human brain tumours, J. Neurol. Sci. 1981 Nov.–Dec.;52(2–3):269–77.

Gaffen, J. D. et al.: Increased killing of malignant cells by giving indomethacin with methotrexate, p. 30; col. 1; XP002084860Chemical Abstract, vol. 106, No. 11, Mar. 16, 1987, abstract No. 78377, J.D.

Gallo–Payet, Nicole et al., Cyclic AMP–independent effects of ACTH on glomerulosa cells of the rat adrenal cortex, J. Steroid Biochem. Mol. Biol. (1999), 69(1–6), 335–342.

Gilman, S.C. et al., Nonsteroidal Anti–inflammatory Drugs in Cancer Therapy, (circa 1985).

Giorgi M. et al., Induction of cyclic AMP and cyclic GMP 3':5'–cyclic nucleotide phosphodiesterase activities in neuroblastoma lines under differentiating conditions, Int. J. Dev. Neurosci. 1997 Jun.;15(3):309–19.

Giorgi, Mauro et al., Characterization of 3':5' cyclic nucleotide phosphodiesterase activities of mouse neuroblastoma N18TG2 cells, FEBS Lett. 324(1) pp. 76–80 (1993).

Glavin, G.B. et al., Toxicology and Applied Pharmacology, vol. 83, pp. 386–389 (1986).

Gonzaga, R.A.F. et al., The Lancet, Mar. 30, 1985, p. 751.

Gudi, T., Huvar, I., Meinecke, M., Lohmann, S. M., Boss, G. R., and Pilz, R. B. Regulation of gene expression by cGMP–dependent protein kinase. Transactivation of the c–fos promoter. J Biol Chem, 271: 4597–600, 1996.

Hagiwara, Masatoshi et al., Effect of 1–(3–chloroanilino)–4–phenylpthalazine (MY–5445), a specific inhibitor of cyclic CMP phosphodiesterase, on human platelet aggregation (Abstract Only), J. Pharmacol. Exp. Ther. 229(2) pp. 467–471 (1984).

Haynes, Johnson, Jr. et al., Erythro–9–(2–hydroxy–3–nonyl) adenine inhibits cyclic–3',5'–guanosine monophosphate–stimulated phosphodiesterase to reverse hypoxic pulmonary vasoconstriction in the perfused rat lung, J. Pharmacol. Exp. Ther. (1996), 276(2), 752–7.

Hidaka, H. et al., Selective Inhibitors of Three Forms of Cyclic Nucleotide Phosphodiesterase—Basic and Potential Clinical Applications, vol. 16, Advances in Cyclic Nucleotide and Protein Phosphorylation Research, pp. 245–259 (1984).

Hucker, H.B. et al., Drug Metabolism & Disposition, vol. 1, No. 6, pp. 721–736 (1973).

Janik, P. et al., Inhibition of Growth of Primary and Metastatic Lewis Lung Carcinoma Cells by the Phosphodiesterase Inhibitor Isobutylmethylxanthine, Cancer Res. vol. 40, pp. 1950–1954, (Jun., 1980).

Jiang, X. et al., Inhibition of calmodulin–dependent phosphodiesterase induces apoptosis in human leukemic cells, Proc. Natl. Acad. Sci. USA, vol. 83, pp. 11236–11241, Oct. 1996.

Kakkar R. et al., Calmodulin–dependent cyclic nucleotide phosphodiesterase (PDE1), Cell Mol. Life Sci. 1999 Jul.;55(8–9):1164–86.

Kodama, K. et al., Effects of a novel, selective and potent phosphodiesterase type V inhibitor, E4021, on myocardial ischemia in guinea pigs, Euro. J. of Pharma. 263, pp. 93–99 (1994).

Korinek, V. et al., Constitutive Transcriptional Activation by a β–Catenin–Tcf Complex in APC$^{-/-}$ Colon Carcinoma, Science, vol. 275, pp. 1784–1786, Mar. 21, 1997.

Kozai, Shigetada et al., Synthesis and biological activity of 9–(2,6–difluorobenzyl)–9H–purines bearing chlorine, Chem. Pharm. Bull. (1999), 47(4), 574–575.

Laasberg T. et al., Nerve growth factor increases the cyclic GMP level and activates the cyclic GMP phosphodiesterase in PC12 cells, FEBS Lett. 1988 Nov. 7;239(2):367–70.

Lange–Carter, C. A., Pleiman, C. M., Gardner, A. M., Blumer, K. J., and Johnson, G. L. A divergence in the MAP kinase regulatory network defined by MEK kinase and Raf. Science, 260: 315–9, 1993.

Law P.Y. et al., delta–Opioid receptor activates cAMP phosphodiesterase activities in neuroblastoma x glioma NG108–15 hybrid cells, Mol. Pharmacol. 1993 May;43(5):684–93.

Leach M.O. et al., Measurements of human breast cancer using magnetic resonance spectroscopy: a review of clinical measurements and a report of localized 31P measurements of response to treatment, NMR Biomed. 1998 Nov.;11(7):314–40.

Li, Y., Maher, P., and Schubert, D. Requirement for cGMP in nerve cell death caused by glutathione depletion. J Cell Biol, 139: 1317–24, 1997.

Lichtner R. et al., Antimetastatic action of RX–RA 69, a new potent PDE–inhibitor in the Lewis lung carcinoma of the mouse, Prog. Clin. Biol. Res. 1982;89:131–41.

Lichtner, R. B. et al., The Pyrimido–pyrimidine Derivatives RA 233 adn RX–RA 85 affect Growth and Cytoskeletal Organization of Rat Mammary Adenocarcinoma Cells, Eur. J. Cancer Clin. Oncol., vol. 23, No. 9, pp. 1269–1275 (1987).

Lichtner, Rosemarie B. et al., The pyrimidopyrimidine derivatives RA233 and RX–RA85 affect cell cycle distribution of two murine tumor cell lines, Eur. J. Cancer Clin. Oncol. 25(6) pp. 945–951 (1989).

Lin, A., Minden, A., Martinetto, H., Claret, F. X., Lange–Carter, C., Mercurio, F., Johnson, G. L., and Karin, M. Identification of a dual specificity kinase that activates the Jun kinases and p38–Mpk2. Science, 268: 286–90, 1995.

Liu, Leo X. et al., Formation of cyclooxygenase–derived eicosanoids by a parasitic intravascular nematode, Adv. Prostaglandin, Thromboxane, Leukotriene Res. (1990), 21B (Prostaglandins Relat. Compd.), 509–12.

Lohmann, S. M., Vaandrager, A. B., Smolenski, A., Walter, U., and De Jonge, H. R. Distinct and specific functions of cGMP–dependent protein kinases. Trends Biochem Sci, 22: 307–12, 1997.

Loweth, A. C., Williams, G. T., Scarpello, J. H., and Morgan, N. G. Evidence for the involvement of cGMP and protein kinase G in nitric oxide–induced apoptosis in the pancreatic B–cell line, HIT–T15. FEBS Lett, 400: 285–8, 1997.

Luginer, C. et al., Selective Inhibition of Cyclic Nucleotide Phosphodiesterases of Human, Bovine and Rat Aorta, Biochem. Pharmacology, vol. 35, No. 10, pp. 1743–1751 (1986).

Mahmoud, N. et al., Apc Gene Mutation is Associated with a Dominant–Negative Effect upon Intestinal Cell Migration, Cancer Research 57, pp. 5045–5050, Nov. 15, 1997.

Mahmoud, N. et al., Genotype–Phenotype Correlation in Murine Apc Mutation: Differences in Enterocyte Migration and Response to Sulindac, Cancer Research 59, pp. 353–359, Jan. 15, 1999.

Makaryan, A.P. et al., Cyclic Nucleotides in Patients with Malignant Neoplasms of the Colon, Laboratornoe Delo, vol. 8, pp. 31–33 (1991).

Mamytbekova, A. et al., Antimetastatic effect of flurbiprofen and other platelet aggregation inhibitors (Abstract Only), Neoplasma 33(4), pp. 417–421 (1986).

Marcoz, P. et al., Modulation of rat thymocyte proliferative response through the inhibition of different cyclic nucleotide phosphodiesterase isoforms by means of selective inhibitors and cGMP–elevating agents (Abstract Only), Mol. Pharmacol. 44(5) pp. 1027–1035 (1993).

Marko D. et al., Induction of apoptosis by an inhibitor of cAMP–specific PDE in malignant murine carcinoma cells overexpressing PDE activity in comparison to their nonmalignant counterparts, Cell Biochem Biophys. 1998;28(2–3):75–101.

Maundrell, K., Antonsson, B., Magnenat, E., Camps, M., Muda, M., Chabert, C., Gillieron, C., Boschert, U., Vial–Knecht, E., Martinou, J. C., and Arkinstall, S. Bcl–2 undergoes phosphorylation by c–Jun N–terminal kinase/stress– activated protein kinases in the presence of the constitutively active GTP–binding protein Rac1. J Biol Chem, 272: 25238–42, 1997.

Mehta, Rajendra et al., Structure–Activity Relationships of Brassinin in Preventing the Development of Carcinogen–Induced Mammary Lesions in Organ Culture, Anticancer Research 14: 1209–1214 (1994).

Mery, Pierre–Francois et al., EHNA as an inhibitor of PDE2: A pharmacological and biochemical study in cardiac myocytes, Phosphodiesterase Inhib. (1996), 81–88.

Michie, Alison M. et al., Rapid regulation of PDE–2 and PDE–4 cyclic AMP phosphodiesterase activity following ligation of the T cell antigen receptor on thymocytes: analysis using the selective inhibitors erythro–9–(2–hydroxy–3–nonyl)–adenine (EHNA) and rolipram, Cell. Signalling (1996), 8(2), 97–110.

Mitchell, J.A. et al., Selectivity of nonsteroidal antiinflammatory drugs as inhibitors of constitutive and inducible cyclooxygenase; Proc. Natl. Acad. Sci. USA, vol. 90, Dec. 1994, pp. 11693–11697.

Molnar–Kimber, K. et al., Modulation of TNFa and IL–1B from indotoxin–stimulated monocytes by selective PDE isozyme inhibitors (Abstract Only), Agents Actions 39(Spec. Conf. Issue), C77–C79 (1993).

Molnar–Kimber, K. L. et al., Differential regulation of TNF–a and IL–1B production from endotoxin stimulated human monocytes by phosphodiesterase inhibitors (Abstract Only), Mediators Inflammation 1(6) pp. 411–417 (1992).

Moorghen, M. et al., Acta Histochemica, Suppl.–Band XXIX, S. 195–199 (1990).

Moorghen, M. et al., Journal of Pathology, vol. 156, pp. 341–347 (1988).

Morgan A.J. et al., Comparison of the effect of isobutylmethylxanthine and phosphodiesterase–selective inhibitors on cAMP levels in SH–SY5Y neuroblastoma cells, Biochem. Pharmacol. 1993 Jun. 22;45(12):2373–80.

Morin, P. et al., Activation of β–Catenin–Tcf Signaling in Colon Cancer by Mutations in β–Catenin or APC, Science, vol. 275, pp. 1787–1789, Mar. 21, 1997.

Murray, K.J. et al., Potential Use of Selective Phosphodiesterase Inhibitors in the Treatment of Asthma, New Drugs for Asthma Therapy, Birkhauser Verlag Basel, pp. 27–46 (1991).

Nagai T. et al., Distinct isozyme patterns of cyclic nucleotide phosphodiesterase in human neuroblastoma and ganglioneuroma; a possible market of differentiation of neural crest–derived tumors and Schwann cells, Jpn. J. Cancer Res. 1986 Jan.; 77(1):52–8.

Nakai A. et al., High activity of cyclic 3',5'–nucleotide phosphodiesterase in sera of patient with phaeochromocytoma, Clin. Endocrinol. (Oxf) 1986 Apr.;24(4):409–14.

Naskalski J.W. et al., Correlation of granulocyte intracellular activities of cyclic nucleotide phosphodiesterases with leukocyte count in patients with chronic myelogenous leukaemia, Haematologia (Budap) 1986;19(4):285–92.

Nichols M.R. et al., Tyrosine kinase–independent inhibition of cyclic–AMP phosphodiesterase by genistein and tryphostin 51, Arch. Biochem. Biophys. 1999 Jun. 15;366(2):224–30.

Nicholson, C.D. et al. Differential modulation of tissue function and therapeutic potential of selective inhibitors of cyclic nucleotide phosphodiesterase isoenzymes, Trends Pharmacol. Sci. (TiPS), vol. 12, pp. 19–27 (1991).

O'Donnell, James M. et al., Behavioral effects of family–selective inhibitors of cyclic nucleotide phosphodiesterases, Pharmacol., Biochem. Behav. (1999), 63(1), 185–192.

Oldham S.B. et al., Presence of calmodulin in parathyroid adenomas, Miner Electrolyte Metab. 1982;7(5):273–80.

Patel, T., Gores, G. J., and Kaufmann, S. H. The role of proteases during apoptosis. Faseb J, 10: 587–97, 1996.

Patel, V. et al., Plasma cAMP and cAMP–phosphodiesterase (PDE) levels in cancer patients before and after surgery, Indian J. Cancer 1981 Sep.;18(3):181–4.

Peifer, M., β–Catenin as Oncogene: The Smoking Gun, Science, vol. 275, pp. 1752–1753, Mar. 21, 1997.

Pepin, P. et al., Effects of Sulindac and Oltipraz on the tumorigenicity of 4–(methylnitrosamino)1–(3–pyridyl)–1–Butanone in A/J mouse lung, Carcinogenesis vol. 13 No. 3 pp. 341–348 (1992).

Porter, Roderick et al., Preparation of 6–phenyl–3–(5–tetrazoly)pyridin–2(H)–one derivatives as cyclic AMP–dependent protein kinase agonists (Abstract Only), PCT Int. Appl. WO9206085 A1, (Sep. 26, 1991).

Radomski, Marek W. et al., Human Colorectal adenocarcinoma cells: differential nitric oxide synthesis determines their ability of aggregate platelets (Abstract Only), Cancer Res. 51(22) pp. 6073–608 (1991).

Raeburn, David et al., Effects of isoenzyme–selective inhibitors of cyclic nucleotide phosphodiesterase on microvascular leak in guinea pig airways in vivo (Abstract Only), J. Pharmacol. Exp. Ther., 267(3), pp. 1147–51 (1993).

Redmond O.M., Tissue characterization and assessment of preoperative chemotherapeutic response in musculoskeletal tumors by in vivo 31P magnetic resonance spectroscopy, Magn. Reson. Med. 1992 Oct.;27(2):226–37.

Rivet–Bastide, Michele et al., cGMP–stimulated cyclic nucleotide phosphodiesterase regulates the Basal calcium current in human atrial myocytes, J. Clin, Invest. (1997), 99(11), 2710–2718.

Rosman, Guy J. et al., Isolation and characterization of human cDNAs encoding a cGMP–stimulated 3',5'–cyclic nucleotide phosphodiesterase, Gene (1997), 191(1), 89–95.

Rubinfeld, B. et al., Stabilization of β–Catenin by Genetic Defects in Melanoma Cell Lines, Science, vol. 275, pp. 1790–1792, Mar. 21, 1997.

Sadhu, Krishna et al., Differential expression of the cyclic GMP–stimulated phosphodiesterase PDE2A in human venous and capillary endothelial cells, J. Histochem. Cytochem. (1999), 47(7), 895–905.

Saeki, T. et al., Isolation of Cyclic Nucleotide Phosphodiesterase Isozymes From Pig Aorta, Biochem. Pharmacology, vol. 46, No. 5, pp. 833–839 (1993).

Sanchez, I., Hughes, R. T., Mayer, B. J., Yee, K., Woodgett, J. R., Avruch, J., Kyriakis, J. M., and Zon, L. I. Role of SAPK/ERK kinase–1 in the stress–activated pathway regulating transcription factor c–Jun. Nature, 372: 794–8, 1994.

Savini F. et al., Phosphodiesterase in human colon carcinoma cell line CaCo–2 in culture, Life Sci. 1995;56(22):PL421–5.

Schlesinger, T. K., Fanger, G. R., Yujiri, T., and Johnson, G. L. The TAO of MEKK. Front Biosci, 3: D1181–6, 1998.

Schudt, Christian et al., "Phosphodiesterase Inhibitors" The Handbook of Immunopharmacology, Academic Press, 1996, pp. 65–134.

Semmler, J. et al., Xanthine derivatives: comparison between suppression of tumor necrosis factor–x production and inhibition of cAMP phosphodiesterase activity, Immunology 78, pp. 520–525 (1993).

Shen, T.Y. et al., Chemical and Biological Studies on Indomethacin, Sulindac and Their Analogs, pp. 170–178 (circa 1975).

Sheth S.B. et al., Isolation and regulation of the cGMP–inhibited cAMP phosphodiesterase in human erythroleukemia cells, Thromb. Haemost 1997 Jan.;77(1):155–62.

Shiah, S. G., Chuang, S. E., Chau, Y. P., Shen, S. C., and Kuo, M. L. Activation of c–Jun NH2–terminal kinase and subsequent CPP32/Yama during topoisomerase inhibitor beta–lapachone–induced apoptosis through an oxidation–dependent pathway. Cancer Res, 59: 391–8, 1999.

Silvola, J. et al., Effects of nonsteroidal anti–inflammatory drugs on rat gastric mucosal phosphodiesterase activity, Agents and Actions, vol. 12.4, pp. 516–520 (1982).

Singh R.P. et al., Plasma c–AMP and c–AMP–PDE activity in carcinoma of uterine cervix, Mater Med. Pol. 1988 Apr.–Jun.;20(2):76–8.

Solntseva T.I. et al., [Some feature of cyclic adenosine monophosphate metabolism in mouse liver and hepatoma 22] (Article in Russian), Biokhimiia 1977 Jul.; 42(7):1331–7.

Souness, John E. et al., Role of Selective cyclic GMP phosphodiesterase inhibition in the myorelaxant actions of M&B 22,943, MY–5445, vinpocetine and 1–methyl–3–isobutyl–8–(methylamino)xanthine (Abstract Only), Br. J. Pharmacol. 98(3) pp. 725–734 (1989).

Srivastava, R. K., Mi, Q. S., Hardwick, J. M., and Longo, D. L. Deletion of the loop region of Bcl–2 completely blocks paclitaxel– induced apoptosis. Proc Natl Acad Sci U S A, 96: 3775–80, 1999.

Stacey, P., Rulten, S., Dapling, A., and Phillips, S. C. Molecular cloning and expression of human cGMP–binding cGMP–specific phosphodiesterase (PDE5). Biochem Biophys Res Commun, 247: 249–54, 1998.

Stevens R.H. et al., Adenosine 3',5'–cyclic monophosphate and guanosine 3',5'–cyclic monophosphate phosphodiesterase activities in 1,2–demethylhydrazine induced colon adenocarcinoma, Cancer Lett. 1979 Aug.;7(4):227–34.

Stevens R.H. et al., Adenosine and guanosine 3',5' cyclic monophosphate phosphodiesterase activities in rat small and large bowel following single and multiple exposure to 1,2–demethylhydrazine, Drug Chem. Toxicol. 1981;4(2):161–72.

Thompson, W. J., Pamukcu, R., Liu, L., Li, H., Ahnen, D., G., S., and Piazza, G. A. Exisulind (Prevatac) induced apoptosis in cultured colonic tumor cells involves inhibition of cyclic GMP (cG) phosphodiesterase (PDE). Proc. Amer. Assoc. Cancer Res, 40: 4, 1999.

Torphy T.J. et al., Stimulation of beta adrenoceptors in a human monocyte cell line (U937) up–regulates cyclic AMP–specific phosphodiesterase activity, J. Pharmacol. Exp. Ther. 1992 Dec.;263(3):1195–205.

Tsou, K–C. et al. 5'–Nucleotide Phosphodiesterase Isozyme–V as a Marker for Liver Metastases in Breast Cancer Patients, Cancer 54:1788–1793, 1984.

Tulshian, D. et al., Synthesis and Phosphodiesterase Activity of Carboxylic Acid Mimetics of Cyclic Guanosine 3",5"–Monophosphate, J. Med. Chem, vol. 36, 1210–1220 (1993).

Turnbull J.L. et al., The isolation and characterization of cyclic nucleotide phosphodiesterases from Morris hepatoma 5123tc(h) and rat liver, Int. J. Biochem. 184;16(1):19–29. No Date Avail.

Turner, N.C. et al., Pulmonary effects of type V cyclic GMP specific phosphodiesterase inhibition in anaesthetized guinea–pig, Br. J. Pharmacol., vol. 111, 1198–1204 (1994).

Turner, N.C. et al., Relaxation of guinea–pig trachea by cyclic AMP phosphodiesterase inhibitors and their enhancement by sodium mitroprusside, Br. J. Pharmacol., vol. 111, pp. 1047–1052 (1994).

Tzanakakis G.N. et al., Prevention of human pancreatic cancer cell–induced hepatic metastasis in nude mice by dipyridamole and its analog RA–233, Cancer 1993 Apr. 15;71(8):2466–71.

Vaandrager, A. B. and de Jonge, H. R. Singalling by cGMP–dependent protein kinases. Mol Cell Biochem, 157: 23–30, 1996.

Van Lookeren Campagne, Michiel M. et al., Characterization of the yeast low Km cAMP–phosphodiesterase with cAMP analogs. Applications in mammalian cells that express the yeast PDE2 gene, J. Biol. Chem. (1990), 265(10), 5847–54.

Verde, Ignacio et al., Characterization of the cyclic nucleotide phosphodiesterase subtypes involved in the regulation of the L–type Ca2+ current in rat ventricular myocytes, Br. J. Pharmacol. (1999), 127(1), 65–74.

Waddell, W.R. et al., Am. J. Surgery, vol. 157, pp. 175–79 (1989).

Waddell, W.R. et al., J. Surg. Oncology, vol. 24, pp. 83–87 (1983).

Weishaar, R.E. et al., A new generation of phosphodiesterase inhibitors: multiple molecular forms of phosphodiesterase and the potential for drug selectivity, J. Med. Chem. 185 May;28(5):537–45. No Date Avail.

Weishaar, R.E. et al., Multiple Molecular Forms of Cyclic Nucleotide Phosphodiesterase in Cardiac and Smooth Muscle and In Platelets, Biochem. Pharmacology, vol. 35, No. 5, pp. 787–800 (1986).

Whalin, Michael E. et al., Phosphodiesterase II, the cGMP–Activatable Cyclic Nucleotide Phosphodiesterase, Regulates Cyclic AMP Metabolism in PC12 Cells, Molecular Pharmacology, 39, pp. 711–717. No Date Avail.

Xin Y., [Relationships between cyclic nucleotide phosphodiesterases (cPDE) and some patho–biologic behaviors of stomach cancer—I. Histochemical studies of CPDE in stomach cancer tissues], (Article in Chinese), Chung Hua Chung Liu Tsa Chih 1989 Mar.; 11(2):117–20.

Yamamoto, K., Ichijo, H., and Korsmeyer, S. J. BCL–2 Is Phosphorylated and Inactivated by an ASK1/Jun N–Terminal Protein Kinase Pathway Normally Activated at G(2)/M. Mol Cell Biol, 19: 8469–8478, 1999.

Yamashita, Nobuyuki et al., Rolipram, a phosphodiesterase–4–selective inhibitor, promotes the survival of cultured rat dopaminergic neurons, Jpn. J. Pharmacol. (1997), 75(2), 155–159.

Yamashita, Nobuyuki et al., Rolipram, a selective inhibitor of phosphodiesterase type 4, pronouncedly enhanced the forskolin–induced promotion of dopamine biosynthesis in primary cultured rat mesencephalic neurons, Jpn. J. Pharmacol. (1997), 71(5), 91–95.

Yasumoto, T. et al., Properties of Base–Substituted and Carboxyl–Esterified Analogues of Griseolic Acid, a Potent cAMP Phosphodiesterase Inhibitor, Biochemical Pharmacology, vol. 43, No. 10, pp. 2073–2081 (1992).

Zacharski, L. R. et al., Effect of Mopidamol on Survival in Carcinoma of the Lung and Colon: Final Report of Veterans Administration Cooperative Study No. 188, J. of the Nat'l. Cancer Inst., vol. 80, No. 2, pp. 90–96 (1988).

Zacher, L. A; Carey, G. B., Cyclic AMP metabolism by swine adipocyte microsomal and plasma membranes, Comp. Biochem. Physiol., Part B: Biochem. Mol. Biol. (1999), 124B(1), 61–71.

Zurbonsen K. et al., Dissociation between phosphodiesterase inhibition and antiproliferative effects of phosphodiesterase inhibitors on the Dami cell line, Biochem. Pharmacol. 1997 Apr. 25;53(8):1141–7.

* cited by examiner

Compound I Induced Growth Inhibition in Androgen Sensitive Prostate Tumor Cells (LNCaP)

8A. in the absence of cGMP    8B. in the presence of 8uM cGMP

← 85Kd

Protein kinase G activity from drug-treated SW480 cell lysates.
SW480 cells were treated with DMSO (0.03%, lanes 1 and 2), Exsulind (200, 400 and 600μM; lanes 3, 4, 5, respectively) and E4021 (0.1, 1 and 10μM, lanes 6, 7, 8, respectively) for 48 hrs.

METHOD FOR SCREENING COMPOUNDS FOR THE TREATMENT OF NEOPLASIA

BACKGROUND OF THE INVENTION

This invention is a method for identifying compounds potentially useful for the selective treatment and prevention of pre-cancerous and cancerous lesions in mammals, as well as pharmaceutical compositions containing such compounds.

For many years, researchers have sought compounds that selectively treat neoplastic cells without substantial growth-inhibiting adverse effects on normal cells. Conventional cancer chemotherapeutics—regardless of the type of cancer against which they have been directed—share one common feature: conventional compositions (e.g. herceptin, taxol, cisplatin, tamoxifen etc), to the extent they have any substantial effects on neoplastic cells—virtually always have significant adverse effects on normal tissues. Many of the side effects are debilitating and life-threatening. Thus, conventional chemotherapeutics are typically administered only after the neoplasia has significantly progressed to the stage where the drug side effects clearly outweigh the risks of no chemotherapy.

Conventional chemotherapeutics also typically are used to treat fairly specific types of neoplasias. For example, leuprolide is commonly prescribed to treat advanced prostate cancer, but not colon or lung cancers. Compositions with activities against broader ranges of neoplasias are desired.

In Pamukcu et al., in U.S. Pat. No. 5,401,774, compounds such as those now known as exisulind are disclosed for anti-neoplastic purposes. Contrary to conventional chemotherapeutics, such compounds are very selective against neoplastic cells as opposed to normal cells. Thus, such compounds can be administered on a chronic basis without the side effects normally associated with conventional chemotherapeutics. In addition, because of their safety profile, such compounds can be administered at the earliest stages of disease. Thus, new compounds have become recognized as a new class of antineoplastics known as selective apoptotic anti-neoplastic drugs ("SAANDs").

Besides outstanding safety advantages over conventional chemotherapeutics, SAANDs also have a wider range of therapeutic application compared to conventional chemotherapeutics. For example, the first SAAND, exisulind, has been reported to have anti-neoplastic effects on colon, breast, lung, prostate, kidney, and melanoma neoplasias. It also has effects on other neoplasias.

SAANDs have the further advantage over anti-neoplastic NSAIDS (e.g., sulindac) because, unlike NSAIDs, SAANDs do not inhibit COXI/II enzymes. Inhibition of COX I and/or COX II enzymes (e.g., by indomethacin, celecoxib and other NSAIDs) lead to considerable side effects when taken on a chronic basis. In addition, COX inhibition is unnecessary for anti-neoplastic efficacy. Not surprisingly, many such COX I and COX II inhibitors also have not been demonstrated to have significant anti-neoplastic activities. The side effects of COX I and COX II inhibitors include gastric irritations that can lead to severe ulceration, and kidney toxicities. Since SAANDs antineoplastic therapy is enhanced with chronic or long-term administration, the COX inhibitors—to the extent any exhibit anti-neoplastic properties—are inappropriate simply because of safety considerations, since few patients can realistically take COX inhibitors chronically or long-term. For inflammation, COX inhibitors are commonly used only on a short-term or acute basis as a result.

How SAANDs can work without the side effects of COX inhibitors (or the even more severe side effects of conventional chemotherapeutics) remained a mystery until recently. As reported in U.S. Pat. No. 5,858,694, SAANDs work, in part by the inhibition of PDE5, which appears to be a necessary part of how SAANDs induce apoptosis (a form of cell death) in neoplastic, but not in normal cells. It was also discovered that SAANDs work by increasing cGMP and reducing cAMP in neoplastic cells, also as reported in the '694 patent.

However, it was later discovered that some PDE5 inhibitors did not induce apoptosis (see, e.g. U.S. patent application Ser. No. 09/173,375 filed Oct. 15, 1998). In the '375 application, the discovery of a new cGMP-specific PDE found in neoplastic cells was first reported. One observation that separated anti-neoplastic PDE5 inhibitors from inactive PDE5 inhibitors was that the anti-neoplastic PDE5 inhibitors inhibited the new cGMP-specific PDE, whereas the inactive PDE5 inhibitors (e.g., sildenafil) had little relative effect. This observation, as disclosed in the '375 application, led to more accurate drug discovery screening methods to identify active, anti-neoplastic PDE5 inhibitors (i.e. additional SAANDs).

However, more accurate and alternative methods to evaluate and identify compounds for their usefulness as SAANDs are desired.

SUMMARY OF THE INVENTION

This invention relates to a novel method for screening and identifying compounds for their usefulness as SAANDs. In particular, this invention provides a method for identifying compounds that can be used to treat and prevent neoplasia, including precancerous lesions, with minimal side effects associated with COX inhibition and other non-specific interactions associated with conventional chemotherapeutics.

In the course of researching why some PDE5 inhibitors induced apoptosis, we discovered that those that do induce apoptosis do so by ultimately activating JNK1 kinase activity. JNK is a proline-directed kinase of the MAP kinase extended family. It is believed that this effect is caused upstream of the JNK apoptotic pathway by the regulation of cGMP and cAMP by pro-apoptotic PDE5 inhibitors, as taught in U.S. Pat. No. 5,858,694 to Piazza et al. This connection between cGMP/cAMP regulation and JNK1 activity was surprising, and forms a useful way of ascertaining whether a cGMP inhibitor is a SAAND. In contrast to this effect on JNK kinase activity, tested SAANDs caused only slight activation of ERK2 kinase activity, a related but separate pathway of signal transduction commonly reported to play a role in stimulating cell proliferation.

This invention involves evaluating whether a compound causes an increase in cGMP-dependent protein kinase G ("PKG") activity and activates JNK1 kinase in neoplastic cells. We believe that the elevation of PKG activity is due at least in part by the increase in cGMP caused by SAANDs inhibition of the appropriate PDEs, as described above.

The other characteristics of SAANDs are (1) inhibition of PDE5 as reported in the '694 patent above, (2) inhibition of the novel cGMP-specific PDE conformation, (3) inhibition of PDE2; (4) the fact that SAANDs increase intracellular cGMP in neoplastic cells, and (5) the fact that they decrease cAMP levels in some types of neoplastic cells.

Thus, one embodiment of the novel method of this invention is evaluating whether a compound activates JNK, causes PKG activity to elevate in neoplastic cells and whether that compound inhibits PDE5. Another embodiment of the novel screening method of this invention is evaluating whether a compound that activates JNK, causes PKG activity to elevate in neoplastic cells and whether that compound inhibits the novel cGMP-specific PDE described above and/or PDE2. Still a third embodiment is evaluating whether a compound activates JNK, causes PKG activity to elevate in neoplastic cells and whether that compound causes cGMP to rise in neoplastic cells and/or causes cAMP levels to fall. Compounds successfully evaluated in such fashions have application as SAANDs.

Among other things, this invention relates to novel in vitro and in vivo methods for selecting compounds for their ability to treat and prevent neoplasia, especially precancerous lesions, safely. In particular, the present invention is a method for selecting compounds that can be used to treat and prevent neoplasia, including precancerous lesions. The compounds so identified can have minimal side effects attributable to COX inhibition and other non-specific interactions associated with conventional chemotherapeutics. The compounds of interest can be tested by exposing neoplastic cells to the cGMP PDE-inhibiting compounds, and if such a compound activates JNK in those cells, the compound is then further evaluated (e.g., in vitro or in vivo animal or human testing models or trials) for its other anti-neoplastic properties (e.g., its ability to induce apoptosis in vitro and/or in vivo).

One aspect of this invention, therefore, involves a screening/selection method to identify a compound effective for treating neoplasia that includes ascertaining the compound's inhibition PDE5 and/or PDE2 and its inhibition of COX. Preferably, the screening and selection methods of this invention further include determining whether the compound inhibits the growth of tumor cells in vitro or in vivo.

By selecting compounds in this fashion, potentially beneficial and improved compounds for treating neoplasia can be identified more rapidly and with greater precision than possible in the past for the purposes of developing pharmaceutical compositions and therapeutically treating neoplasia. Further benefits will be apparent from the following detailed description.

This invention also includes pharmaceutical compositions containing such compounds, as well as therapeutic methods involving such compounds.

BRIEF DESCRIPTION OF THE DRAWINGS

FIGS. 1 A–C illustrate the activation of JNK1 and caspase-3 in SW480 colon cancer cells exposed to sulindac sulfide and several SAANDs.

FIG. 2A SW480 cells were treated with either DMSO (–) or Compound A, 0.1 $\mu$M; dbcGMP, 500 $\mu$M; YC-1, 50 $\mu$M; MY-5445, 50 $\mu$M; dipyridamole, 10 $\mu$M or dbcAMP, 500 $\mu$M for one hour. The cells were lysed, JNK1 immunoprecipitated, and the IP assayed for in vitro kinase activity as described in FIG. 1A.

FIG. 2B SW480 cells were pre-treated with either DMSO, KT5720 (2 $\mu$M) or Rp-8-pCPT-cGMPS (2 $\mu$M) for 2 hours and then treated with Compound B (0, 1 or 10 $\mu$M) for one hour. The cells were lysed and assayed for JNK1 activation in the IP as described above.

FIG. 3A: SW480 cells were treated with Compound A (1 $\mu$M), collected at the indicated time points, and cell lysates assayed for SEK1 activation by Western blotting with anti-phospho-SEK1 (Thr223) antibody. Fold increase in phosphorylation was measured by densitometry. The experiment was repeated three times with similar results.

FIG. 3B: SW480 cells were treated with Compound A (1 $\mu$M) and collected after either 1 or 2 days and the cell lysates were assayed for MEKK1 cleavage by Western blotting with anti-MEKK1 antibody. Minus (–) indicates DMSO treated control cells.

DETAILED DESCRIPTION OF THE PREFERRED EMBODIMENTS

I. The Characteristics of SAANDs

Figure 1A:
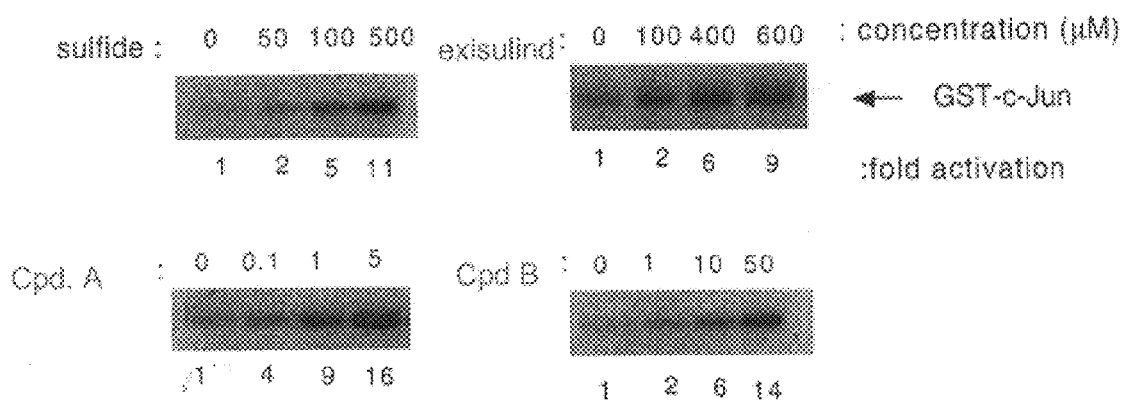
FIG. 1A: SW480 cells were treated with either DMSO (–) or the indicated concentrations ($\mu$M) of sulindac sulfide, exisulind, Compound A or Compound B, for one hour. The cells were lysed, JNK1 immunoprecipitated with an anti-JNK1 antibody, and the immunoprecipitate ("IP") assayed for in vitro kinase activity with GST-c-Jun(1-79) as the substrate. The experiments were repeated three times with similar results. Fold activation was measured using a Phosphor Imager.

A. c-Jun and JNK—In General c-Jun is a component of the transcription factor AP-1, which is activated by a wide variety of extracellular stimuli. The regulation of c-Jun is complex and is believed to involve both increases in the levels of c-Jun protein as well as phosphorylation of specific serines (63 and 73) by Jun N-terminal kinase (JNK).

JNK activation has been associated with apoptosis, previously. For example, Gajate C et al. Mol Pharmacol, April 1998, 53:4, 602–12 found that the ether phospholipid 1-O-octadecyl-2-O-methyl-rac-glycero-3-phosphocholine ("ET-18-OCH3")—a potent inducer of apoptosis in human tumor cells—induced apoptosis in a manner associated with activation of JNK signaling. Specifically they showed that the addition of ET-18-OCH3 to distinct human leukemic cells (HL-60, U937, and Jurkat), which undergo rapid apoptosis on treatment with ET-18-OCH3, induced a dramatic and sustained increase in the of c-jun mRNA level that was associated with activation of activator protein-1 transcription factor. They found that ET-18-OCH3 induced a persistent activation of JNK in HL-60 cells that was detected before the onset of apoptosis, the latter being assessed by DNA fragmentation and by the appearance of phosphatidylserine on the external leaflet of the plasma membrane. The inductions of JNK after HL-60 monocyte/macrophage differentiation and ET-18-OCH3-mediated apoptosis were distinguished by the different activation patterns, transient versus persistent, respectively. ET-18-OCH3 analogues unable to induce apoptosis failed to activate JNK. ET-18-OCH3-dependent JNK activation was not detected in K562 cells, which did not undergo apoptosis on treatment with ET-18-OCH3. Phorbol myristate acetate inhibited both ET-18-OCH3-induced apoptosis and sustained JNK activation; thus, persistent JNK activation by ET-18-OCH3 was associated with the capacity of that ether phospholipid to induce apoptosis. Furthermore, antisense oligonucleotides directed against c-jun blocked ET-18-OCH3-induced apoptosis, indicating a role for c-Jun in the apoptotic response to ET-18-OCH3.

Similarly Li Y, et al, Mol Cell Biol, August 1998, 18:8, 4719–31 reported that UV-stimulated JNK1 activation promoted UV-induced SCLC apoptosis.

Those reports and others indicate that JNK activation and c-Jun can represent a pathway to the induction of apoptosis.

B. Summary of Confirmatory Experiments About the Role of SAANDs the JNK Pathway As explained above, like the non-steroidal anti-inflammatory drug sulindac, SAANDs such as exisulind (Aptosyn) causes regression and inhibits the recurrence of polyps in patients with familial adenomatous polyposis (FAP). Exisulind also inhibits carcinogenesis in rodents and causes growth inhibition and apoptosis in a variety of human cancer cell lines. Exisulind does not, however, inhibit cyclooxygenase COX-1 or 2. In U.S. Pat. Nos. 6,156,528 and 6,200,771 (which are incorporated herein by reference), it was disclosed that exisulind and other SAANDs act by inhibiting cGMP-hydrolyzing phosphodiesterases (PDE2/5) in neoplastic cells, resulting in an increase in protein kinase G ("PKG") in neoplastic cells.

In this invention, we discovered that one of the unexpected effects of the resulting increase in cGMP induced by SAANDs in neoplastic cells was an effect on signal transduction in the JNK pathway. Further confirmation of this observation, we found that sulindac sulfide, exisulind and two other SAANDS, Compound A ([(Z)-5-fluoro-2-methyl-(3,4,5-trimethyl-oxybenzylidene)-3-(N-benzyl)-indenylacetamide]) and Compound B ((Z)-5-fluoro-2-methyl-(4-pyridylidene)-3-(N-benzyl)indenylacetamide hydrochloride), caused rapid and sustained activation of the c-Jun amino-terminal kinase 1 ("JNK1") in SW480 colon cancer cells exposed to such drugs, and in several other types of cancer cells exposed to such drugs as discussed below.

To verify this novel characteristic of SAANDs, since one of the effects of SAANDs on neoplastic cells is to increase cGMP level in such cells, we found that other compounds known to increase cellular levels of cGMP also activated JNK1 in neoplastic cells. In addition because one of the effect of SAANDs treatment is to increase PKG activity, we discovered that an inhibitor of PKG, Rp-8-pCPT-cGMPS, inhibited JNK1 activation in neoplastic cells exposed to both the PKG inhibitor and an anti-neoplastic cGMP-specific PDE inhibitor such as sulindac sulfide and SAANDs.

Activation of SEK1 and MEKK1, which are upstream of JNK1, were also observed when neoplastic cells were exposed to SAANDs. The PKG antagonist Rp-8-pCPT-cGMPS also inhibited sulindac-induced cleavage of PARP, a marker of apoptosis. Thus the elevation of cGMP levels caused by exisulind and SAANDs induce apoptosis, at least in part, through activation of PKG which then activates the MEKK1-SEK1-JNK1 cascade. These studies also implicate, for the first time, a role for cGMP in the JNK pathway.

Recent studies indicate that SAANDs are specific inhibitors of cGMP-specific phosphodiesterases 2 and 5 (PDE2/5), as reported in the above patent applications. Based on these findings, two potent SAANDs, Compounds A and B, have been found to be specific inhibitors of PDE5/2. Inhibition of PDE5/2 by SAANDs induces an increase in intracellular levels of cGMP, as set forth in U.S. patent application Ser. Nos. 09/046,739 and 09/414,626. These findings indicate that elevation of intracellular levels of cGMP may be an important mechanism for triggering apoptosis, but not all of the downstream signaling pathways have been identified.

In the experiments reported herein, we found that SAANDs cause a rapid and sustained activation of JNK1 which we believe is mediated by cGMP-stimulated activation of PKG. These studies also implicate for the first time a role for PKG in activation of JNK1.

C. Experimental Procedures and Results—JNK Activity

SW480 human colon cancer cells were treated with either the solvent DMSO or a cGMP-specific PDE inhibitors (i.e., sulindac sulfide, 50–500 $\mu$M; exisulind, 100–600 $\mu$M; Compound A, 0.1–5 $\mu$M; and Compound B, 1–50 $\mu$M) for one hour and assayed for JNK1 activation. These concentrations were chosen since they provided optimal induction of apoptosis. Endogenous JNK1 was immunoprecipitated with anti-JNK1 antibody and in vitro kinase assays were performed with GST-c-Jun(1-79) as the substrate. As shown in FIG. 1A, sulindac sulfide, exisulind and Compounds A and B activated JNK1. The fold-induction was quantitated by phosphor imager analysis and is indicated in FIG. 1A. Even at very low doses, the potent SAANDs, compounds A and B, activated JNK1 more strongly than did sulindac sulfide or exisulind. Similar effects were observed in other colon cancer cell lines including HCT116 and HT29 (data not shown).

Figure 1B:
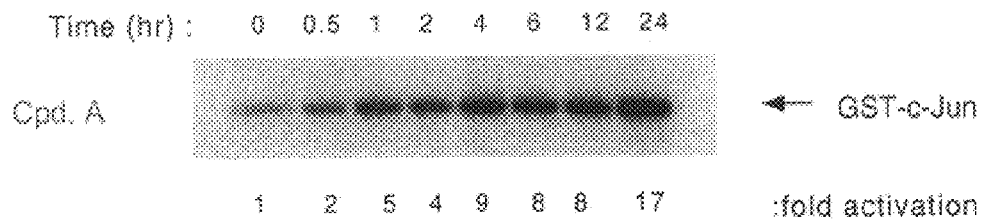
FIG. 1B: SW480 cells were treated with Compound A (1 $\mu$M) for the indicated time periods and in vitro JNK1 kinase activity was determined as described above.
Figure 1C:
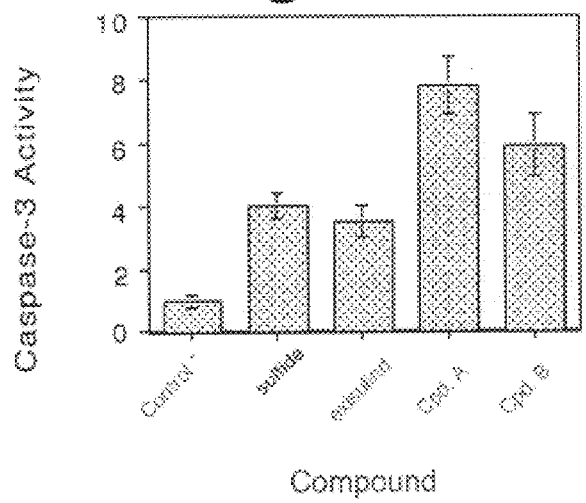
FIG. 1C: SW480 cells were treated with sulindac sulfide (200 $\mu$M), exisulind (600 $\mu$M), Compound A (1 $\mu$M) or Compound B (10 $\mu$M) for 24 hours. The cells were lysed and the extracts assayed for caspase-3 activity using Ac-DEVD-AFC as the substrate, in the presence or absence of the caspase-3 inhibitor Ac-DEVD-CHO. Caspase-3 activity was calculated by subtracting the AFC fluorescence (excitation; 400 nm, emission; 505 nm) in the presence of Ac-DEVD-CHO from the AFC fluorescence in the absence of Ac-DEVD-CHO.

A time course study indicated that when SW480 cells were treated with Compound A (1 $\mu$M) JNK1 activation was sustained for at least 24 hours (FIG. 1B). We then confirmed the apoptotic activity of these compounds by measuring caspase-3 activity after treating SW480 cells with similar concentrations of sulindac sulfide, exisulind, Compound A or Compound B for 24 hours. Protein extracts were then prepared and caspase-3 activity was measured with Ac-DEVD-AFC as the substrate, in the presence or absence of the caspase-3 inhibitor Ac-DEVD-CHO. FIG. 1C shows that the treatment of SW480 cells with all of these compounds led to activation of caspase-3. Similar findings were obtained with HCT116 and HT29 cells (data not shown).

Figure 2A:
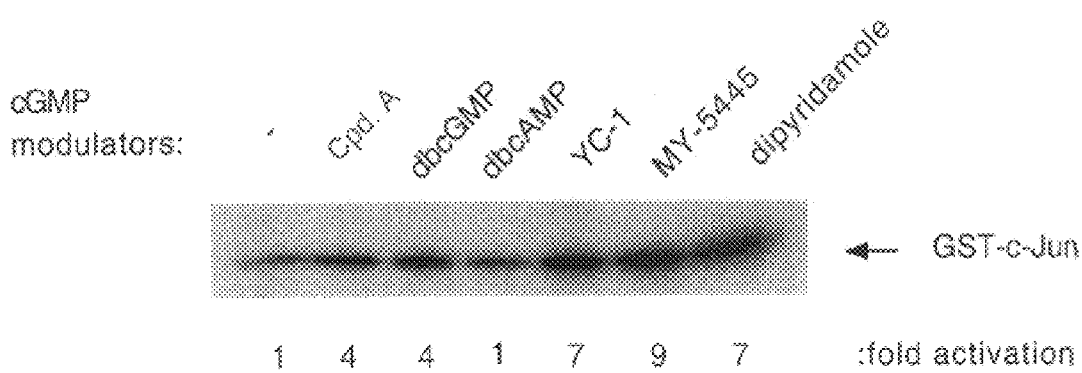
FIGS. 2A–B illustrate the activation of JNK1 by cGMP modulators and the role of PKG.

We then examined the effect of an elevation of cGMP levels on JNK1 activity in SW480 cells. The intracellular level of cGMP is positively regulated by guanylate cyclase and negatively regulated by phosphodiesterase 2 and 5 (PDE2/5), as taught in the aforesaid U.S. Patent Applications (8, 9). We treated SW480 cells with various cGMP modulators for one hour and then collected protein extracts for JNK1 assays (FIG. 2A). Dibutyrylguanosine 3':5'-cyclic monophosphate ("dbcGMP"; 500 $\mu$M), a cell-permeable cGMP analog, activated JNK1 in SW480 cells, but the cell permeable cAMP analog dibutyryladenosine 3':5'-cyclic monophosphate (dbcAMP; 500 $\mu$M) was inactive. YC-1 (50 $\mu$M), a guanylate cyclase activator, also activated JNK1. MY-5445 (50 $\mu$M) and dipyridamole (10 $\mu$M), PDE5-specific inhibitors, also activated JNK1 in SW480 cells. Similar activation of JNK1 by these cGMP modulators was observed in HCT116 and HT29 cells (data not shown). These results show that elevation of cGMP levels, by various means, leads to activation of JNK1 in colon cancer cells. The signal appears to be specific for cGMP and not cAMP since dbcGMP but not dbcAMP activated JNK1 in these cells.

Figure 2B:
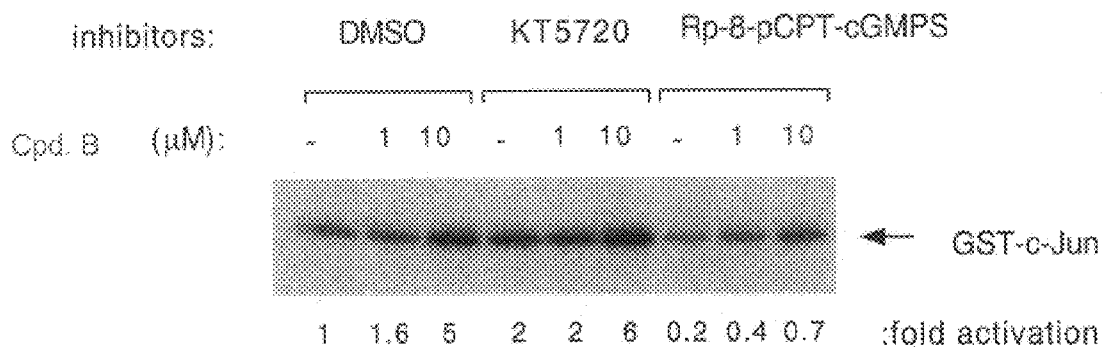

PKG is one of the major cellular targets of cGMP, and the binding of cGMP, or the above-mentioned analog, activates PKG activity, both in vivo and in vitro. However, the precise role of PKG in signal transduction pathways is not known. Since the results of the experiments leading to the present invention indicated that factors that increase cGMP lead to activation of JNK1, we tested whether a PKG-specific inhibitor, Rp-8-pCPT-cGMP, could inhibit the ability of a SAAND to induce JNK1 activation. As a control, KT5720 was used as a protein kinase A ("PKA")-specific inhibitor. SW480 cells were treated with either DMSO, KT5720 (2 $\mu$M) or Rp-8-pCPT-cGMPS (2 $\mu$M) for 2 hours and then treated with either DMSO or Compound B (1 or 10 $\mu$M) for one hour. Cell extracts were collected and assayed for JNK1 activation. As shown in FIG. 2B, Rp-8-pCPT-cGMP strongly inhibited Compound B-induced JNK1 activation, while KT5720 had no inhibitory activity. Taken together, these results show that SAANDs activate JNK1 through a cGMP/PKG pathway.

Figure 3A:
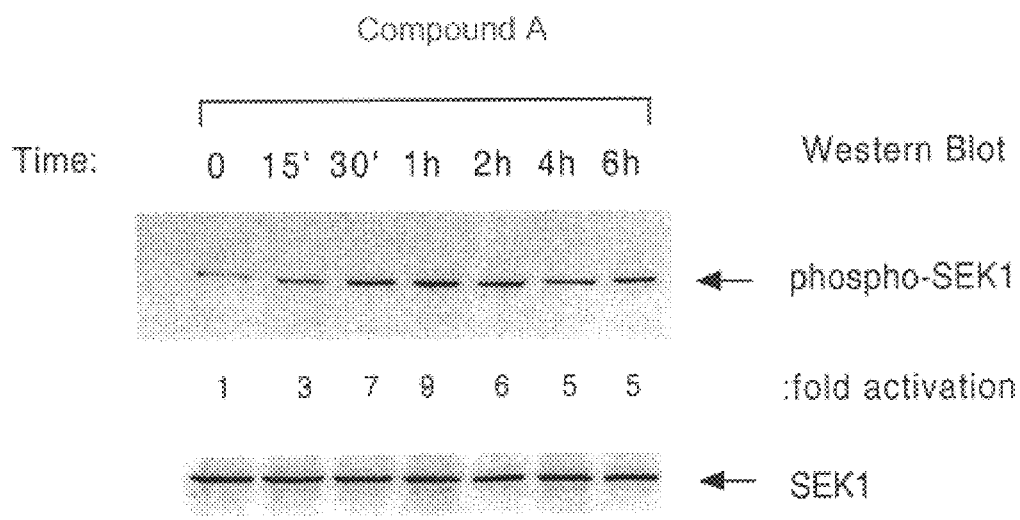
FIGS. 3A–B illustrate the activation of the MEKK1-SEK1 pathway by a SAAND.

To further characterize the signal transduction pathway involved in the above-described JNK1 activation, we tested whether SEK1, the protein kinase immediately upstream of JNK1, was also activated by a SAAND. Activation of SEK1 occurs through phosphorylation of two residues of this protein, Ser219 and Thr223, by the protein kinase MEKK1. SW480 cells were treated with Compound A (1 $\mu$M) for various times, up to 6 hours, and extracts were analyzed by Western blot analysis using a phospho-Thr223-specific SEK1 antibody. The treatment with Compound A induced increased phosphorylation of SEK1, within 15–30 minutes, without changing the total cellular level of the endogenous SEK1 protein (see, FIG. 3A). By 1 hour there was a 9-fold induction, and this effect persisted for at least 6 hours (FIG. 3A). Treatment of the cells with only the DMSO solvent did not induce phosphorylation of SEK1 (data not shown).

Figure 3B:
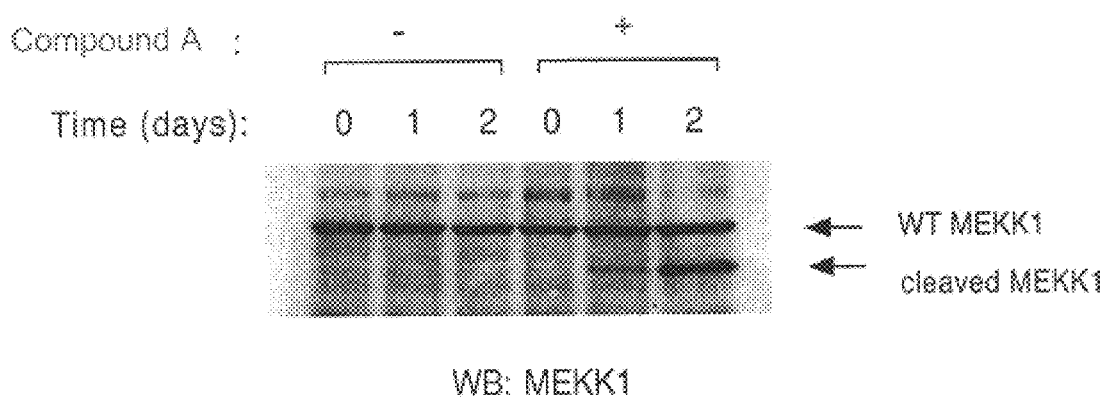

We then examined the effect of a SAAND on MEKK1, a protein kinase immediately upstream of SEK1. Western blot analysis for the MEKK1 protein revealed cleavage of this protein after the treatment of SW480 cells with Compound A for one or two days, but no cleavage was seen when the cells were treated with DMSO (FIG. 3B). Previous studies indicate that MEKK1 is cleaved during activation by caspases (19). We also observed strong and transient activation of MEKK1 activity by Compound A as determined by MEKK1 autophosphorylation and phosphorylation of GST-SEK1. These data suggest that SAANDs activate JNK1 though the MEKK1-SEK1 pathway. It is not clear, however, whether cGMP-activated PKG directly activates MEKK1 or whether the cleavage and activation of MEKK1 is an indirect effect of the process of apoptosis.

Figure 4:
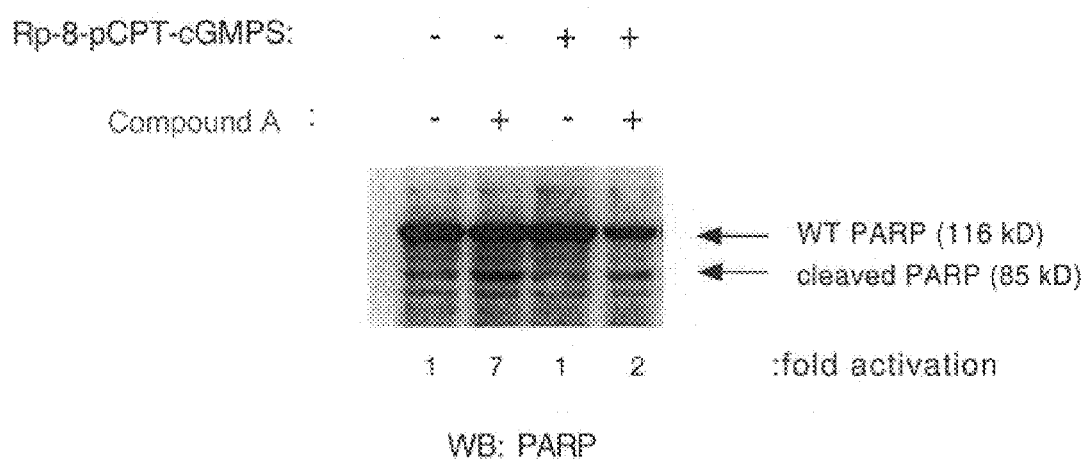
FIG. 4 illustrates the inhibition of Compound A-induced PARP cleavage by Rp-8-pCPT-cGMPS. SW480 cells were pre-treated with either DMSO (–) or Rp-8-pCPT-cGMPS (2 $\mu$M) for 2 hours and then treated with either DMSO (–) or Compound A (1 $\mu$M). Both the floating and attached cells were collected after 2 days, and the cell lysates were assayed for PARP cleavage by Western blotting with anti-PARP antibody. Fold increase in PARP cleavage was measured by densitometry of the 85 kD fragment.

Finally, we investigated whether activation of the PKG pathway is required for the induction of apoptosis by SAANDs. SW480 cells were treated with either DMSO or the PKG inhibitor Rp-8-pCPT-cGMPS (2 $\mu$M) for 2 hours and then the cells were treated with either DMSO or Compound A (1 $\mu$M) for 2 days. Both the floating and attached cells were collected, and the cell lysates were assayed for poly (ADP-ribose) polymerase (PARP) cleavage by Western blotting with an anti-PARP antibody. PARP is a 116 kD nuclear enzyme that converts NAD to nicotinamide and protein-linked ADP-ribose polymers, which are important for DNA repair and genomic maintenance. In cells that are undergoing apoptosis the 116 kD PARP protein is cleaved by caspase-3 into 85 and 25 kD fragments, thus resulting in loss of normal PARP function. This inactivation of PARP apparently prevents depletion of cellular levels of NAD and ATP, which are thought to be required for later events in apoptosis. As shown in FIG. 4, Compound A induced PARP cleavage, but this cleavage was significantly inhibited by pre-incubation of the cells with the PKG inhibitor Rp-8-pCPT-cGMPS. We also observed that expression of a dominant negative JNK1 protein in SW480 cells strongly inhibited Compound A-induced cleavage of PARP. These data provide evidence that the cGMP/PKG/JNK1 pathway plays a critical role in the apoptosis induced by this SAAND in SW480 cells.

Thus, in these experiments, we show, for the first time, that SAANDs and other cGMP-inducing agents activate the JNK1 pathway of signal transduction and provide evidence that this pathway plays a critical role in the apoptosis induced by these compounds. A scheme based on the present results in shown in FIG. 5.

Figure 5:
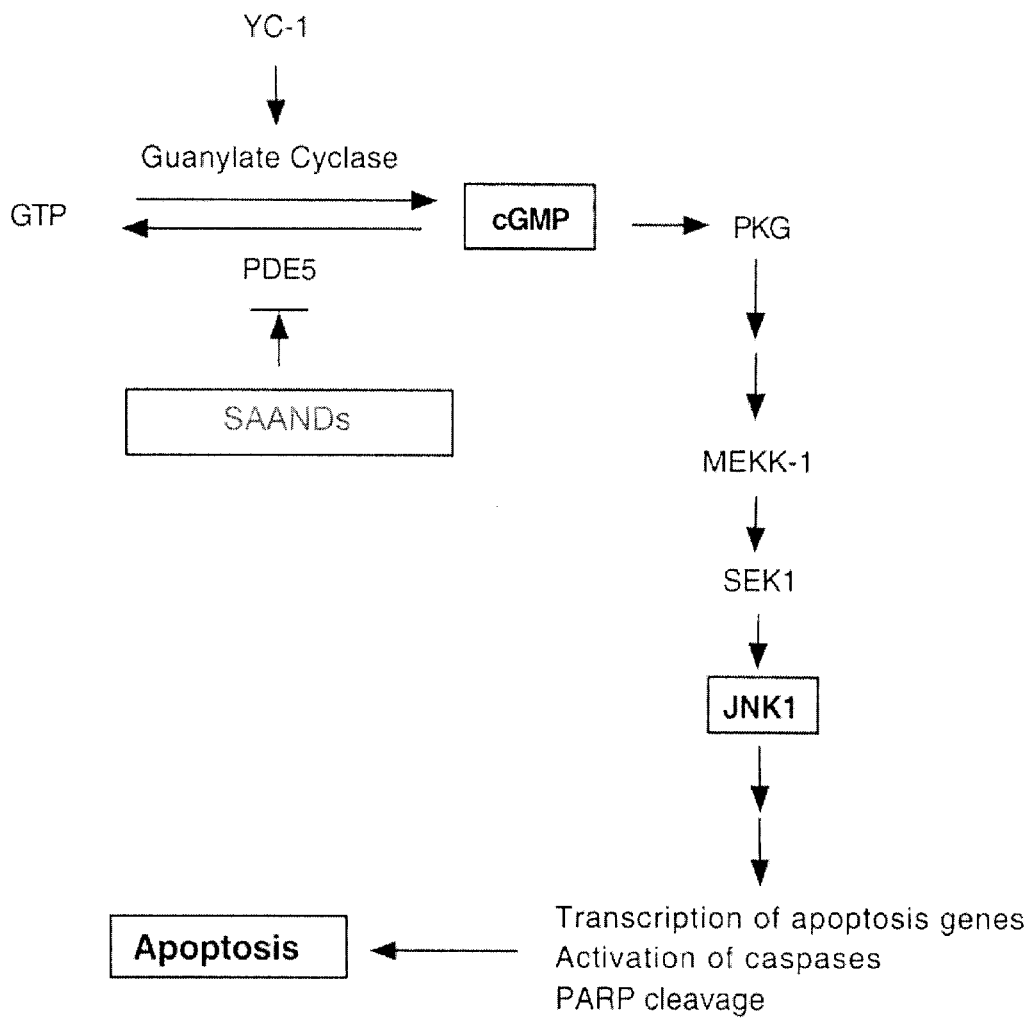
FIG. 5 illustrates the apoptotic signal transduction pathways activated by SAANDs. SAANDs induce an increase in intracellular levels of cGMP through inhibition of PDE2/5. This activates PKG that leads to activation of the MEKK-1/SEK1/JNK1 pathway. Activation of JNK1 then plays a role, perhaps together with other signals, in activation of caspases, PARP cleavage and other events that mediate apoptosis.

In U.S. patent applications Ser. Nos. 09/414,626 and 09/216,070, it was shown that exisulind (Aptosyn), and the two potent derivatives Compounds A and B, inhibit cGMP-specific phosphodiesterase 2 and 5 in SW480 cells and other cancer-derived cell lines, thus causing increased cellular levels of cGMP. This leads to activation of PKG as taught in U.S. patent application Ser. No. 09/414,628. The activation of PKG leads, within 30–60 min, to persistent phosphorylation and activation of SEK1 which, in turn, leads to rapid and persistent activation of JNK1, as shown in FIG. 5. We believe that the activation of JNK1 then leads to activation of caspases, the cleavage of PARP and the transcription of genes that also contribute to the program of apoptosis, as previously described for other non-SAANDs apoptotic agents that activate JNK1. Several investigators have reported that JNK1 is involved in apoptotic signaling pathways triggered by various agents, including UV and γ radiation, benzyl isothiocyanate, and the DNA topoisomerase inhibitor β-lapachone. But none of these methods is reported to involve cGMP or PKG.

JNK1 activates the AP-1 transcription factor and thereby induces several genes involved in apoptosis. It also phosphorylates bcl-2 and thus inactivates its anti-apoptotic activity. It seems likely that the activation of PKG also influences other pathways that may contribute to the growth inhibitory and apoptotic effects of SAANDs. These studies provide the first evidence implicating PKG in the JNK1 pathway of signal transduction, thus expanding the role of this enzyme system in signal transduction and the control of gene expression.

D. Further Confirmation That SAANDs Increase PKG Activity In Neoplastic Cells

Using the PKG assay described below, the following experiments were performed to establish that SAANDs increase PKG activity due either to increase in PKG expression or an increase in cGMP levels (or both) in neoplastic cells treated with a SAAND.

Two different types of PDE inhibitors were evaluated for their effects on PKG in neoplastic cells. A SAAND, exisulind, was evaluated since it is anti-neoplastic. Also, a non-SAAND classic PDE5 inhibitor, E4021, was evaluated to ascertain whether PKG elevation was simply due to classic PDE5 inhibition, or whether PKG elevation was involved in the pro-apoptotic effect of SAANDs inhibition of PDE5 and the novel PDE disclosed in U.S. patent application Ser. No. 09/173,375 to Liu et al filed Oct. 15, 1998.

To test the effect of cGMP-specific PDE inhibition on neoplasia containing the APC mutation, SW480 colon cancer cells were employed. SW 480 is known to contain the APC mutation. About 5 million SW480 cells in RPMI 5% serum are added to each of 8 dishes:

2–10 cm dishes—30 $\mu$L DMSO vehicle control (without drug),

3–10 cm dishes—200 $\mu$M, 400 $\mu$M, 600 $\mu$M exisulind in DMSO, and

3–10 cm dishes—E4021; 0.1 $\mu$M, 1 $\mu$M and 10 $\mu$M in DMSO.

The dishes are incubated for 48 hrs at 37° C. in 5% $CO_2$ incubator.

The liquid media are aspirated from the dishes (the cells will attach themselves to the dishes). The attached cells are washed in each dish with cold PBS, and 200 $\mu$L cell lysis buffer (i.e., 50 mM Tris-HCl, 1% NP-40, 150 mM NaCl, 1 mM EDTA, 1 mM $Na_3VO_4$, 1 mM NaF, 500 $\mu$M IBMX with proteinase inhibitors) is added to each dish. Immediately after the cell lysis buffer is added, the lysed cells are collected by scraping the cells off each dish. The cell lysate from each dish is transferred to a microfuge tube, and the microfuge tubes are incubated at 4° C. for 15 minutes while gently agitating the microfuge tubes to allow the cells to lyse completely. After lysis is complete, the microfuge tubes are centrifuged full speed (14,000 r.p.m.) for 15 minutes. The supernatant from each microfuge tube is transferred to a fresh microfuge tube.

A protein assay is then performed on the contents of each microfuge tube because the amount of total protein will be greater in the control than in the drug-treated samples, if the drug inhibits cell growth. Obviously, if the drug does work, the total protein in the drug-treated samples should be virtually the same as control. In the above situation, the control and the E-4021 microfuge tubes needed dilution to normalize them to the high-dose exisulind-treated samples (the lower dose groups of exisulind had to be normalized to the highest dose exisulind sample). Thus, after the protein assays are performed, the total protein concentration of the various samples must be normalized (e.g., by dilution).

For each drug concentration and control, two PKG assays are performed, one with added cGMP, and one without added cGMP, as described in detail below. The reason for performing these two different PKG assays is that cGMP specifically activates PKG. When PKG activity is assayed using the novel PKG assay of this invention, one cannot ascertain whether any increase the PKG activity is due to increased cGMP in the cells (that may be caused by cGMP-specific PDE inhibition) or whether the PKG activity level is due to an increased expression of PKG protein. By determining PKG activity in the same sample both with and without added cGMP, one can ascertain whether the PKG activity increase, if any, is due to increased PKG expression. Thus, if an anti-neoplastic drug elevates PKG activity relative to control, one can establish if the drug-induced increase is due to increased PKG protein expression (as opposed to activation) in the drug-treated sample if (1) the drug-treated sample with extra cGMP exhibits greater PKG activity compared to the control sample with extra cGMP, and (2) the drug-treated sample without extra cGMP exhibits greater PKG activity relative to control.

After, parallel samples with and without added cGMP are prepared, 50 $\mu$L of each cell lysate is added to 20 $\mu$L of the PDE5/GST solid phase substrate slurry described above. For each control or drug cell lysate sample to be evaluated, the reaction is started by adding phosphorylation buffer containing 10 $\mu$Ci $^{32}$P-$\gamma$-ATP solution (200 $\mu$M ATP, 4.5 mM MgCl; 5 mM $KH_2PO_4$; 5 mM $K_2HPO_4$;) to each mixture. The resultant mixtures are incubated at 30° C. for 30 minutes. The mixtures are then centrifuged to separate the solid phase, and the supernatant is discarded. The solid phase in each tube is washed with 700 $\mu$L cold PBS. To the solid phase, Laemmli sample buffer (Bio-Rad) (30 $\mu$L) is added. The mixtures are boiled for 5 minutes, and loaded onto 7.5% SDS-PAGE. The gel is run at 150 V for one hour. The bands obtained are stained with commassie blue to visualize the 85 Kd GST-PDE5 fusion protein bands, if present. The gel is dried, and the gel is laid on x-ray film which, if the PDE5 is phosphorylated, the film will show a corresponding darkened band. The darkness of each band relates to the degree of phosphorylation.

Figure 8:
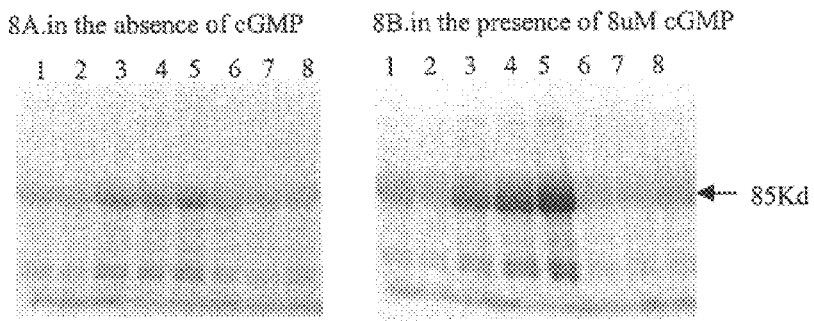
FIG. 8A is a SDS (X-ray film exposure) protein gel PKG assay of SW480 cell lysates from drug-treated cell lysates in the absence of added cGMP, where cells were treated in culture for 48 hours with DMSO (0.03%, lanes 1 and 2), exisulind (200, 400 and 600 $\mu$M; lanes 3, 4, 5) and E4021 (0.1, 1 and 10 $\mu$M, lanes 6, 7, 8).
FIG. 8B is a SDS (X-ray film exposure) protein gel PKG assay of SW480 cell lysates from drug-treated cell lysates in the presence of added cGMP, where cells were treated in culture for 48 hours with DMSO (0.03%, lanes 1 and 2), exisulind (200, 400 and 600 $\mu$M; lanes 3, 4, 5) and E4021 (0.1, 1 and 10 $\mu$M, lanes 6, 7, 8).

As shown in FIGS. 8A and 8B, the SAAND exisulind causes PKG activity to increase in a dose-dependent manner in both the samples with added cGMP and without added cGMP relative to the control samples with and without extra cGMP. This is evidenced by the darker appearances of the 85 Kd bands in each of the drug-treated samples. In addition, the SW480 samples treated with exisulind show a greater PKG phosphorylation activity with added cGMP in the assay relative to the samples treated with exisulind alone (i.e. no added cGMP). Thus, the increase in PKG activity in the drug-treated samples is not due only to the activation of PKG by the increase in cellular cGMP when the SAAND inhibits cGMP-specific PDE, the increase in PKG activity in neoplasia harboring the APC mutation is due to increased PKG expression as well.

Also the fact that the E4021-treated SW480 samples do not exhibit PKG activation relative to control (see FIGS. 8A and 8B) shows that the increased PKG activation caused by SAANDs in neoplasia containing the APC mutation is not simply due to inhibition of classic PDE5.

As an analytic technique for evaluating PKG activation, instead of x-ray film exposure as described above, the 85 Kd band from the SDS page can be evaluated for the degree of phosphorylation by cutting the band from the gel, and any $^{32}$P incorporated in the removed band can be counted by scintillation (beta) counter in the $^{32}$P window.

To test the effect of cGMP-specific PDE inhibition on neoplasia containing the β-catenin mutation, HCT116 colon cancer cells were employed. HCT116 is known to contain the β-catenin mutation, but is known not to contain the APC mutation.

The same procedure is used to grow the HCT116 cells as is used in the SW480 procedure described above. In this experiment, only exisulind and controls were used. The exisulind-treated cells yielded PKG that was phosphorylated to a greater extent than the corresponding controls, indicating that PKG activation occurred in the drug-treated cells that is independent of the APC mutation.

Thus, for the purposes of the present invention, we refer to "reducing β-catenin" in the claims to refer to wild type and/or mutant forms of that protein.

E. Confirmation of Increased PKG Expression and Decreased β-Catenin In SW 480 By Western Blot As demonstrated above, SAANDs cause an increase in PKG expression and an increase in cGMP level, both of which cause an increase in PKG activity in SAANDs-treated neoplastic cells. This increase in PKG protein expression was further verified by relatively quantitative western blot, as described below.

SW480 cells treated with exisulind as described previously are harvested from the microfuge tubes by rinsing once with ice-cold PBS. The cells are lysed by modified RIPA buffer for 15 minutes with agitation. The cell lysate is spun down in a cold room. The supernatants are transferred to fresh microcentrifuge tubes immediately after spinning. BioRad DC Protein Assay (Temecula, Calif.) is performed to determine the protein concentrations in samples. The samples are normalized for protein concentration, as described above.

50 μg of each sample is loaded to 10% SDS gel. SDS-PAGE is performed, and the proteins then are transferred to a nitrocellulose membrane. The blotted nitrocellulose membrane are blocked in freshly prepared TBST containing 5% nonfat dry milk for one hour at room temperature with constant agitation.

A goat-anti-PKG primary antibody is diluted to the recommended concentration/dilution in fresh TBST/5% nonfat dry milk. The nitrocellulose membrane is placed in the primary antibody solution and incubated one hour at room temperature with agitation. The nitrocellulose membrane is washed three times for ten minutes each with TBST. The nitrocellulose membrane is incubated in a solution containing a secondary POD conjugated rabbit anti-goat antibody for 1 hour at room temperature with agitation. The nitrocellulose membrane is washed three times for ten minutes each time with TBST. The detection is performed by using Boehringer Mannheim BM blue POD substrate.

Figure 9:
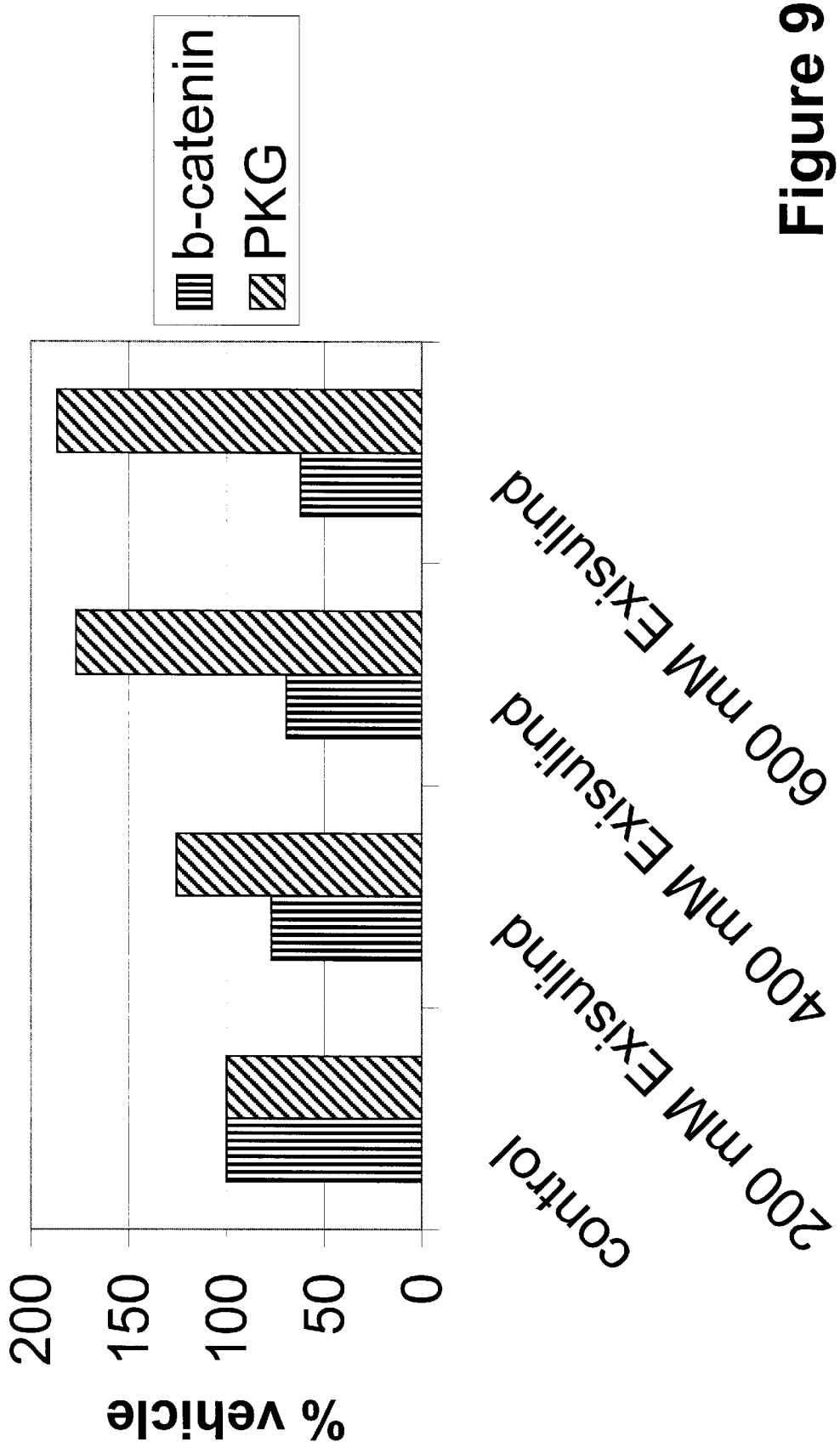
FIG. 9 is a bar graph of the results of Western blot experiments of the effects of exisulind on β-catenin and PKG levels in neoplastic cells relative to control.

As graphically illustrated in FIG. 9, exisulind causes the drop of β-catenin and the increase of PKG, which data were obtained by Western blot. SW480 cells were treated with exisulind or vehicle (0.1% DMSO) for 48 hours. 50 μg supernatant of each cell lysates were loaded to 10% SDS-gel and blotted to nitrocellulose membrane, and the membrane was probed with rabbit-anti-β-catenin and rabbit anti-PKG antibodies.

F. SAANDs Reduce β-Catenin Levels in Neoplastic Cells

This observation was made by culturing SW480 cells with either 200, 400 or 600 μM exisulind or vehicle (0.1% DMSO). The cells are harvested 48 hours post treatment and processed for immunoblotting. Immuno-reactive protein can be detected by Western blot. Western blot analysis demonstrated that expression of β-catenin was reduced by 50% in the exisulind-treated cells as compared to control. These results indicate that β-catenin is reduced by SAANDs treatment. Together with the results above establishing PKG activity increases with such treatment and the results below establishing that β-catenin is phosphorylated by PKG, these results indicate that the reduction of β-catenin in neoplastic cells is initiated by activation of PKG. Thus, using PKG activity in neoplasia as a screening tool to select compounds as anti-neoplastics is useful.

G. The Phosphorylation of β-catenin By PKG

In vitro PKG phosphorylates β-catenin. The experiment that established this involves immunoprecipitating the β-catenin-containing complex from SW480 cells (not treated with any drug) in the manner described below under "β-catenin immunoprecipitation" The immunoprecitated complex, while still trapped on the solid phase (i.e., beads) is mixed with $^{32}$P-γ-ATP and pure PKG (100 units). Corresponding controls with out added PKG are prepared.

The protein is released from the solid phase by SDS buffer, and the protein-containing mixture is run on a 7.5%SDS-page gel. The running of the mixture on the gel removes excess $^{32}$P-γ-ATP from the mixture. Any $^{32}$P-γ-ATP detected in the 93 Kd β-catenin band, therefore, is due to the phosphorylation of the β-catenin. Any increase in $^{32}$P-γ-ATP detected in the 93 Kd β-catenin band treated with extra PKG relative to the control without extra PKG, is due to the phosphorylation of the β-catenin in the treated band by the extra PKG.

The results we obtained were that there was a noticeable increase in phosphorylation in the band treated with PKG as compared to the control, which exhibited minimal, virtually undetectable phosphorylation. This result indicates that β-catenin can be phosphorylated by PKG.

H. The Phosphorylation of Mutant β-catenin By PKG

The same procedure described in the immediately preceding section was performed with HCT116 cells, which contain no APC mutation, but contain a β-catenin mutation. The results of those experiments also indicate that mutant β-catenin is phosphorylated by PKG.

Thus, for the purposes of the present invention, we refer to the phosphorylation of β-catenin in the claims to refer to the phosphorylation of wild type and/or mutant forms of that protein.

I. β-Catenin Precipitates With PKG

Supernatants of both SW480 and HCT116 cell lysates are prepared in the same way described above in the Western Blot experiments. The cell lysate are pre-cleared by adding 150 μl of protein A Sepharose bead slurry (50%) per 500 μg of cell lysate and incubating at 4° C. for 10 minutes on a tube shaker. The protein A beads are removed by centrifugation at 14,000×g at 4° C. for 10 minutes. The supernatant are transferred to a fresh centrifuge tube. 10 μg of the rabbit polyclonal anti-β-catenin antibody (Upstate Biotechnology, Lake Placid, N.Y.) are added to 500 μg of cell lysate. The cell lysate/antibody mixture is gently mixed for 2 hours at 4° C. on a tube shaker. The immunocomplex is captured by adding 150 μl protein A Sepharose bead slurry (75 μl packed beads) and by gently rocking the mixture on a tube shaker for overnight at 4° C. The Sepharose beads are collected by pulse centrifugation (5 seconds in the microcentrifuge at 14,000 rpm). The supernatant fraction is discarded, and the beads are washed 3 times with 800 μl ice-cold PBS buffer. The Sepharose beads are resuspended in 150 μl 2×sample buffer and mixed gently. The Sepharose beads are boiled for 5 minutes to dissociate the immunocomplexes from the beads. The beads are collected by centrifugation and SDS-PAGE is performed on the supernatant.

A Western blot is run on the supernatant, and the membrane is then probed with an rabbit anti β-catenin antibody.

Then the membrane is washed 3 times for 10 minutes each with TBST to remove excess anti β-catenin antibody. A goat, anti-rabbit antibody conjugated to horseradish peroxidase is added, followed by 1 hour incubation at room temperature. When that is done, one can visualize the presence of β-catenin with an HRPO substrate. In this experiment, we could clearly visualize the presence of β-catenin.

To detect PKG on the same membrane, the anti-β-catenin antibody conjugate is first stripped from the membrane with a 62 mM tris-HCl buffer (pH 7.6) with 2% SDS and 100 μM 2β-mercaptoethanol in 55° C. water bath for 0.5 hour. The stripped membrane is then blocked in TBST with 5% non-fat dried milk for one hour at room temperature while agitating the membrane. The blocked, stripped membrane is then probed with rabbit polyclonal anti-PKG antibody (Calbiochem, LaJolla, Calif.), that is detected with goat, anti-rabbit second antibody conjugated to HRPO. The presence of PKG on the blot membrane is visualized with an HRPO substrate. In this experiment, the PKG was, in fact, visualized. Given that the only proteins on the membrane are those that immunoprecipitated with β-catenin in the cell supernatants, this result clearly establishes that PKG was physically linked to the protein complex containing the β-catenin in the cell supernatants.

The same Western blot membrane was also probed after stripping with anti-GSK3-β antibody to ascertain whether it also co-precipitated with β-catenin. In that experiment, we also detected GSK3-β on the membrane, indicating that the GSK3-β precipitated with the GSK3-β and PKG, suggesting that the three proteins may be part of the same complex. Since GSK3-β and β-catenin form part of the APC complex in normal cells, this that PKG may be part of the same complex, and may be involved in the phosphorylation of β-catenin as part of that complex.

II. Screening Pharmaceutical Compositions Using the Invention

A. In General

JNK in combination with PKG or the PDE2s with or without PDE5 to identify compounds that can be used to treat or prevent neoplasms, and that are not characterized by serious side effects.

Cancer and precancer may be thought of as diseases that involve unregulated cell growth. Cell growth involves a number of different factors. One factor is how rapidly cells proliferate, and another involves how rapidly cells die. Cells can die either by necrosis or apoptosis depending on the type of environmental stimuli. Cell differentiation is yet another factor that influences tumor growth kinetics. Resolving which of the many aspects of cell growth is affected by a compound is important to the discovery of a relevant target for pharmaceutical therapy. Screening assays based on this technology can be combined with other tests to select compounds that have growth inhibiting and pro-apoptotic activity.

This invention evolved from the discovery that desirable inhibitors of tumor cell growth induce premature death of cancer cells by apoptosis (see, Piazza, G. A., et al., *Cancer Research,* 55(14), 3110–16, 1995). In addition, it was unexpectedly discovered compounds that selectively induce apoptosis without substantial COX inhibition also inhibit PDE5/2. In particular, and contrary to leading scientific studies, desirable compounds for treating neoplastic lesions inhibit PDE5 (EC 3.1.4.17). PDE5 is one of at least ten gene families of phosphodiesterase. PDE5 and the novel PDE of this invention are unique in that they selectively degrade cyclic GMP and not cAMP, while the other families of PDE selectively degrade/hydrolyze cAMP and not cGMP or non-selectively degrade both cGMP and cAMP.

B. JNK Screening

As explained above, compounds can be evaluated for their ability to activate JNK in neoplastic cells using the methods described above.

C. PKG Screening

A novel assay is employed to assay for PKG activity, which is used in the screening methods of this invention. For explanation purposes, it is useful to describe the PKG assay first, before describing how PKG activity can be useful in drug evaluation in ascertaining whether a compound is potentially useful in the treatment of neoplasia.

The novel PKG assay involves binding to a solid phase plural amino acid sequences, each of which contain at least the cGMP binding domain and the phosphorylation site of phosphodiesterase type 5 ("PDE5"). That sequence is known and described in the literature below. Preferably, the bound PDE5 sequence does not include the catalytic domain of PDE5 as described below. One way to bind the PDE5 sequences to a solid phase is to express those sequences as a fusion protein of the PDE5 sequence and one member of an amino acid binding pair, and chemically link the other member of that amino acid binding pair to a solid phase (e.g., beads). One binding pair that can be used is glutathione S-transferase ("GST") and glutathione ("GSH"), with the GST being expressed as a fusion protein with the PDE5 sequence described above, and the GSH bound covalently to the solid phase. In this fashion, the PDE5 sequence/GST fusion protein can be bound to a solid phase simply by passing a solution containing the fusion protein over the solid phase, as described below.

RT-PCR method is used to obtain the cGB domain of PDE5 with forward and reverse primers designed from bovine PDE5A cDNA sequence (McAllister-Lucas L. M. et al, *J. Biol. Chem.* 268, 22863–22873, 1993) and the selection among PDE 1–10 families. 5'-3', Inc. kits for total RNA followed by oligo (dT) column purification of mRNA are used with HT-29 cells. Forward primer (GAA-TTC-TGT-TAG-AAA-AGC-CAC-CAG-AGA-AAT-G, 203–227) and reverse primer (CTC-GAG-CTC-TCT-TGT-TTC-TTC-CTC-TGC-TG, 1664–1686) are used to synthesize the 1484 bp fragment coding for the phosphorylation site and both low and high affinity cGMP binding sites of human PDE5A (203–1686 bp, cGB-PDE5). The synthesized cGB-PDE5 nucleotide fragment codes for 494 amino acids with 97% similarity to bovine PDE5A. It is then cloned into pGEX-5X-3 glutathione-S-transferase (GST) fusion vector (Pharmacia Biotech )with tac promoter, and EcoRI and XhoI cut sites. The fusion vector is then transfected into *E. Coli* BL21 (DE3) bacteria (Invitrogen). The transfected BL21 bacteria is grown to log phase and then IPTG is added as an inducer. The induction is carried at 20° C. for 24 hrs. The bacteria are harvested and lysated. The soluble cell lysate is incubated with GSH conjugated Sepharose 4B (GSH-Sepharose 4B). The GST-cGB-PDE5 fusion protein can bind to the GSH-Sepharose beads and the other proteins are washed off from beads with excessive cold PBS.

The expressed GST-cGB-PDE5 fusion protein is displayed on 7.5% SDS-PAGE gel as a 85 Kd protein. It is characterized by its cGMP binding and phosphorylation by protein kinases G and A. It displays two cGMP binding sites and the $K_d$ is 1.6±0.2 μM, which is close to $K_d$=1.3 μM of the native bovine PDE5. The GST-cGB-PDE5 on GSH conjugated sepharose beads can be phosphorylated in vitro by cGMP-dependent protein kinase and cAMP-dependent protein kinase A. The $K_m$ of GST-cGB-PDE5 phosphorylation by PKG is 2.7 μM and Vmax is 2.8 μM, while the $K_m$ of BPDEtide phosphorylation is 68 μM. The phosphorylation by PKG shows one molecular phosphate incorporated into one GST-cGB-PDE5 protein ratio.

To assay a liquid sample believed to contain PKG using the PDE5-bound solid phase described above, the sample and the solid phase are mixed with phosphorylation buffer containing $^{32}$P-γ-ATP. The solution is incubated for 30 minutes at 30° C. to allow for phosphorylation of the PDE5 sequence by PKG to occur, if PKG is present. The solid phase is then separated from solution (e.g., by centrifugation or filtration) and washed with phosphate-buffered saline ("PBS") to remove any remaining solution and to remove any unreacted $^{32}$P-γ-ATP.

The solid phase can then be tested directly (e.g., by liquid scintillation counter) to ascertain whether $^{32}$P is incorporated. If it does, that indicates that the sample contained PKG since PKG phosphorylates PDE5. If the PDE5 is bound via fusion protein, as described above, the PDE5-containing fusion protein can be eluted from the solid phase with SDS buffer, and the eluent can be assayed for $^{32}$P incorporation. This is particularly advantageous if there is the possibility that other proteins are present, since the eluent can be processed (e.g., by gel separation) to separate various proteins from each other so that the fusion protein fraction can be assayed for $^{32}$P incorporation. The phosphorylated fusion protein can be eluted from the solid phase with SDS buffer and further resolved by electrophoresis. If gel separation is performed, the proteins can be stained to see the position(s) of the protein, and $^{32}$P phosphorylation of the PDE5 portion of the fusion protein by PKG can be measured by X-ray film exposure to the gel. If $^{32}$P is made visible on X-ray film, that indicates that PKG was present in the original sample contained PKG, which phosphorylated the PDE5 portion of the fusion protein eluted from the solid phase.

Preferably in the assay, one should add to the assay buffer an excess (e.g., 100 fold) of protein kinase inhibitor ("PKI") which specifically and potently inhibits protein kinase A ("PKA") without inhibiting PKG. Inhibiting PKA is desirable since it may contribute to the phosphorylation of the PKG substrate (e.g., PDE5). By adding PKI, any contribution to phosphorylation by PKA will be eliminated, and any phosphorylation detected is highly likely to be due to PKG alone.

A kit can be made for the PKG assay, which kit contains the following pre-packaged reagents in separate containers:

1. Cell lysis buffer: 50 mM Tris-HCl, 1% NP-40, 150 mM NaCl, 1 mM EDTA, 1 mM Na$_3$VO$_4$, 1 mM NaF, 500 μM IBMX, proteinase inhibitors.
2. Protein kinase G solid phase substrate: recombinant GST-cGB-PDE5 bound Sepharose 4B (50% slurry).
3. 2× Phosphorylation buffer: $^{32}$P-γ-ATP (3000 mCi/mmol, 5~10 μCi/assay), 10 mM KH$_2$PO$_4$, 10 mM K$_2$HPO$_4$, 200 μM ATP, 5 mM MgCl$_2$.
4. PKA Protein Kinase I Inhibitor Disposable containers and the like in which to perform the above reactions can also be provided in the kit.

From the above, one skilled in the analytical arts will readily envision various ways to adapt the assay formats described to still other formats. In short, using at least a portion of PDE5 (or any other protein that can be selectively phosphorylated by PKG), the presence and relative amount (as compared to a control) of PKG can be ascertained by evaluating phosphorylation of the phosphorylatable protein, using a labeled phosphorylation agent.

D. COX Screening

A preferred embodiment of the present invention involves determining the cyclooxygenase inhibition activity of a given compound, and determining the cGMP PDE inhibitory activity of the compound. The test compounds are assessed for their ability to treat neoplastic lesions either directly or indirectly by comparing their activities against known compounds useful for treating neoplastic lesions. A standard compound that is known to be effective for treating neoplastic lesions without causing gastric irritation is 5-fluoro-2-methyl-1-(p-methylsulfonylbenzylidene)-3-indenylacetic acid ("exisulind"). Other useful compounds for comparative purposes include those that are known to inhibit COX, such as indomethacin and the sulfide metabolite of sulindac: 5-fluoro-2-methyl-1-(p-methylsulfinylbenzylidene)-3-indenylacetic acid ("sulindac sulfide"). Other useful compounds for comparative purposes include those that are known to inhibit (cGMP-specific PDEs, such as 1-(3-chloroanilino)-4-phenyphthalazine ("MY5445").

As used herein, the term "precancerous lesion" includes syndromes represented by abnormal neoplastic, including dysplastic, changes of tissue. Examples include dysplastic growths in colonic, breast, prostate or lung tissues, or conditions such as dysplastic nevus syndrome, a precursor to malignant melanoma of the skin. Examples also include, in addition to dysplastic nevus syndromes, polyposis syndromes, colonic polyps, precancerous lesions of the cervix (i.e., cervical dysplasia), esophagus, lung, prostatic dysplasia, prostatic intraneoplasia, breast and/or skin and related conditions (e.g., actinic keratosis), whether the lesions are clinically identifiable or not.

As used herein, the terms "carcinoma" or "cancer" refers to lesions which are cancerous. Examples include malignant melanomas, breast cancer, prostate cancer and colon cancer. As used herein, the terms "neoplasia" and "neoplasms" refer to both cancerous and pre-cancerous lesions.

As used herein, the abbreviation PG represents prostaglandin; PS represents prostaglandin synthetase; PGE$_2$ represents prostaglandin E$_2$; PDE represents phosphodiesterase; COX represents cyclooxygenase; cyclic nucleotide, RIA represents-radioimmunoassay.

COX inhibition by a compound can be determined by either of two methods. One method involves measuring PGE$_2$ secretion by intact HL-60 cells following exposure to the compound being screened. The other method involves measuring the activity of purified cyclooxygenases (COXs) in the presence of the compound. Both methods involve protocols previously described in the literature, but preferred protocols are set forth below.

Compounds can be evaluated to determine whether they inhibit the production of prostaglandin E$_2$ ("PGE$_2$"), by measuring PGE$_2$. Using an enzyme immunoassay (EIA) kit for PGE$_2$, such as commercially available from Amersham, Arlington Heights, Ill. U.S.A. Suitable cells include those that make an abundance of PG, such as HL-60 cells. HL-60 cells are human promyelocytes that are differentiated with DMSO into mature granulocytes (see, Collins, S. J., Ruscetti, F. W., Gallagher, R. E. and Gallo, R. C., "Normal Functional Characteristics of Cultured Human Promyelocytic Leukemia Cells (HL-60) After Induction of Differentiation By Dimethylsulfoxide", *J. Exp. Med.,* 149:969–974, 1979). These differentiated cells produce PGE$_2$ after stimulation with a calcium ionophore, A23187 (see, Kargman, S., Prasit, P. and Evans, J. F., "Translocation of HL-60 Cell 5-Lipoxygenase", *J. Biol. Chem.,* 266: 23745–23752, 1991). HL-60 are available from the ATCC (ATCC:CCL240). They can be grown in a RPMI 1640 medium supplemented with 20% heat-inactivated fetal bovine serum, 50 U/mL penicillin and 50 μg/mL streptomycin in an atmosphere of 5% CO$_2$ at 37° C. To induce myeloid differentiation, cells are exposed to 1.3% DMSO for 9 days and then washed and resuspended in Dulbecco's phosphate-buffered saline at a concentration of $3 \times 10^6$ cells/mL.

The differentiated HL-60 cells ($3 \times 10^6$ cells/mL) are incubated for 15 minutes at 37° C. in the presence of the compounds tested at the desired concentration. Cells are then stimulated by A23187 ($5 \times 10^{-6}$ M) for 15 minutes. $PGE_2$ secreted into the external medium is measured as described above.

As indicated above, a second method to assess COX inhibition of a compound is to measure the COX activity in the presence of a test compound. Two different forms of cyclooxygenase (COX-I and COX-2) have been reported in the literature to regulate prostaglandin synthesis. COX-2 represents the inducible form of COX while COX-I represents a constitutive form. COX-I activity can be measured using the method described by Mitchell et al. ("Selectivity of Nonsteroidal Anti-inflammatory Drugs as Inhibitors of Constitutive and Inducible Cyclooxygenase," *Proc. Natl. Acad. Sci. USA.*, 90:11693–11697, 1993, which is incorporated herein by reference) using COX-I purified from ram seminal vesicles as described by Boopathy & Balasubramanian, "Purification And Characterization Of Sheep Platelet Cyclooxygenase" (*Biochem. J.*, 239:371–377, 1988, which is incorporated herein by reference). COX-2 activity can be measured using COX-2 purified from sheep placenta as described by Mitchell et al., 1993, supra.

The cyclooxygenase inhibitory activity of a drug can be determined by methods known in the art. For example, Boopathy & Balasubramanian, 1988, supra, described a procedure in which prostaglandin H synthase 1 (Cayman Chemical, Ann Arbor, Mich.) is incubated at 37° C. for 20 minutes with 100 μM arachidonic acid (Sigma Chemical Co.), cofactors (such as 1.0 mM glutathione, 1.0 mM hydroquinone, 0.625 μM hemoglobin and 1.25 mM $CaCl_2$ in 100 mM Tris-HCl, pH 7.4) and the drug to be tested. Following incubation, the reaction can be terminated with trichloroacetic acid. After stopping the reaction by adding thiobarbituric acid and malonaldehyde, enzymatic activity can then be measured spectrophotometrically at 530 nm.

Obviously, a compound that exhibits a lower COX-I or COX-2 inhibitory activity in relation to its greater combined PDE5/novel PDE/PDE2 inhibitory activities may be a desirable compound.

The amount of COX inhibition is determined by comparing the activity of the cyclooxygenase in the presence and absence of the test compound. Residual (i.e., less than about 25%) or no COX inhibitory activity at a concentration of about 100 μM is indicative that the compound should be evaluated further for usefulness for treating neoplasia.

E. Determining Phosphodiesterase Inhibition Activity

Compounds can be screened for inhibitory effect on the activity of the novel phosphodiesterase of this invention using either the enzyme isolated as described above, a recombinant version, or using the novel PDE and/or PDE2 together with PDE5. Alternatively, cyclic nucleotide levels in whole cells are measured by RIA and compared to untreated and zaprinast-treated cells.

Phosphodiesterase activity can be determined using methods known in the art, such as a method using radioactive $^3$H cyclic GMP (cGMP)(cyclic 3',5'-guanosine monophosphate) as the substrate for the PDE enzyme. (Thompson, W. J., Teraski, W. L., Epstein, P. M., Strada, S. J., *Advances in Cyclic Nucleotide Research*, 10:69–92, 1979, which is incorporated herein by reference). In brief, a solution of defined substrate $^3$H-cGMP specific activity (0.2 μM; 100,000 cpm; containing 40 mM Tris-HCl (pH 8.0), 5 mM $MgCl_2$ and 1 mg/mL BSA) is mixed with the drug to be tested in a total volume of 400 μl. The mixture is incubated at 30° C. for 10 minutes with isolated PDE of this invention. Reactions are terminated, for example, by boiling the reaction mixture for 75 seconds. After cooling on ice, 100 μl of 0.5 mg/mL snake venom (O. Hannah venom available from Sigma) is added and incubated for 10 minutes at 30° C. This reaction is then terminated by the addition of an alcohol, e.g. 1 mL of 100% methanol. Assay samples are applied to 1 mL Dowex 1-X8 column; and washed with 1 mL of 100% methanol. The amount of radioactivity in the breakthrough and the wash from the column is combined and measured with a scintillation counter. The degree of phosphodiesterase inhibition is determined by calculating the amount of radioactivity in drug-treated reactions and comparing against a control sample (a reaction mixture lacking the tested compound but with drug solvent).

Alternatively, the ability of desirable compounds to inhibit the phosphodiesterases of this invention is reflected by an increase in cGMP in neoplastic cells exposed to a compound being screened. The amount of PDE activity can be determined by assaying for the amount of cyclic GMP in the extract of treated cells using radioimmunoassay (RIA). In this procedure, HT-29 or SW-480 cells are plated and grown to confluency. As indicated above, SW-480 contains both PDE5 and the PDE2s, so when PDE activity is evaluated in this fashion, a combined cGMP hydrolytic activity is assayed simultaneously. The test compound is then incubated with the cell culture at a concentration of compound between about 200 μM to about 200 μM. About 24 to 48 hours thereafter, the culture media is removed from the cells, and the cells are solubilized. The reaction is stopped by using 0.2N HCl/50% MeOH. A sample is removed for protein assay. Cyclic GMP is purified from the acid/alcohol extracts of cells using anion-exchange chromatography, such as a Dowex column. The cGMP is dried, acetylated according to published procedures, such as using acetic anhydride in triethylamine, (Steiner, A. L., Parker, C. W., Kipnis, D. M., *J. Biol. Chem.*, 247(4):1106–13, 1971, which is incorporated herein by reference). The acetylated cGMP is quantitated using radioimmunoassay procedures (Harper, J., Brooker, G., *Advances in Nucleotide Research*, 10:1–33, 1979, which is incorporated herein by reference). lodinated ligands (tyrosine methyl ester) of derivatized cyclic GMP are incubated with standards or unknowns in the presence of antisera and appropriate buffers. Antiserum may be produced using cyclic nucleotide-haptene directed techniques. The antiserum is from sheep injected with succinyl-cGMP-albumin conjugates and diluted 1/20,000. Dose-interpolation and error analysis from standard curves are applied as described previously (Seibert, A. F., Thompson, W. J., Taylor, A., Wilbourn, W. H., Barnard, J. and Haynes, J., *J. Applied Physiol.*, 72:389–395, 1992, which is incorporated herein by reference).

In addition, the culture media may be acidified, frozen (−70° C.) and also analyzed for cGMP and cAMP.

In addition to observing increases in the content of cGMP in neoplastic cells caused by desirable compounds, decreases in content of cAMP have also been observed. It has been observed that a particularly desirable compound (i.e., one that selectively induces apoptosis in neoplastic cells, but not substantially in normal cells) follows a time course consistent with cGMP-specific PDE inhibition as one initial action resulting in an increased cGMP content within minutes. Secondarily, treatment of neoplastic cells with a desirable anti-neoplastic compound leads to decreased cAMP content within 24 hours. The intracellular targets of drug actions are being studied further, but current data support the concept that the initial rise in cGMP content and the subsequent fall in cAMP content precede apoptosis in neoplastic cells exposed to desirable compounds.

The change in the ratio of the two cyclic nucleotides may be a more accurate tool for evaluating desirable cGMP-specific phosphodiesterase inhibition activity of test compounds, rather than measuring only the absolute value of cGMP, only cGMP-specific phosphodiesterase inhibition, or only the level of cGMP hydrolysis. In neoplastic cells not treated with anti-neoplastic compounds, the ratio of cGMP content/cAMP content is in the 0.03–0.05 range (i.e., 300–500 fmol/mg protein cGMP content over 6000–8000 fmol/mg protein cAMP content). After exposure to desirable anti-neoplastic compounds, that ratio increases several fold (preferably at least about a three-fold increase) as the result of an initial increase in cyclic GMP and the later decrease in cyclic AMP.

Specifically, it has been observed that particularly desirable compounds achieve an initial increase in cGMP content in treated neoplastic cells to a level of cGMP greater than about 500 fmol/mg protein. In addition, particularly desirable compounds cause the later decrease in cAMP content in treated neoplastic cells to a level of cAMP less than about 4000 fmol/mg protein.

To determine the content of cyclic AMP, radioimmunoassay techniques similar to those described above for cGMP are used. Basically, cyclic nucleotides are purified from acid/alcohol extracts of cells using anion-exchange chromatography, dried, acetylated according to published procedures and quantitated using radioimmunoassay procedures. Iodinated ligands of derivatized cyclic AMP and cyclic GMP are incubated with standards or unknowns in the presence of specific antisera and appropriate buffers.

Verification of the cyclic nucleotide content may be obtained by determining the turnover or accumulation of cyclic nucleotides in intact cells. To measure intact cell cAMP, $^3$H-adenine pre-labeling is used according to published procedures (Whalin, M. E., Garrett Jr., R. L., Thompson, W. J., and Strada, S. J. "Correlation of cell-free brain cyclic nucleotide phosphodiesterase activities to cyclic AMP decay in intact brain slices", *Sec. Mess. and Phos. Protein Research,* 12:311–325, 1989, which is incorporated herein by reference). The procedure measures flux of labeled ATP to cyclic AMP and can be used to estimate intact cell adenylate cyclase or cyclic nucleotide phosphodiesterase activities depending upon the specific protocol. Cyclic GMP accumulation was too low to be studied with intact cell pre-labeling according to published procedures (Reynolds, P. E., S. J. Strada and W. J. Thompson, "Cyclic GMP Accumulation In Pulmonary Microvascular Endothelial Cells Measured By Intact Cell Prelabeling," *Life Sci.,* 60:909–918, 1997, which is incorporated herein by reference).

The PDE inhibitory activity effect of a compound can also be determined from a tissue sample. Tissue biopsies from humans or tissues from anesthesized animals are collected from subjects exposed to the test compound. Briefly, a sample of tissue is homogenized in 500 µl of 6% TCA. A known amount of the homogenate is removed for protein analysis. The remaining homogenate is allowed to sit on ice for 20 minutes to allow for the protein to precipitate. Next, the homogenate is centrifuged for 30 minutes at 15,000 g at 4° C. The supernatant is recovered, and the pellet recovered. The supernatant is washed four times with five volumes of water saturated diethyl ether. The upper ether layer is discarded between each wash. The aqueous ether extract is dried in a speed vac. Once dried, the sample can be frozen for future use, or used immediately. The dried extract is dissolved in 500 µl of assay buffer. The amount of cGMP-specific inhibition is determined by assaying for the amount of cyclic nucleotides using RIA procedures as described above.

The amount of inhibition is determined by comparing the activity of the PDE in the presence and absence of the compound. Inhibition of the cGMP PDEs described above is indicative that the compound is useful for treating neoplasia. Significant inhibitory activity greater than that of the benchmark, exisulind, preferably greater than 50% at a concentration of 10 µM or below, is indicative that a compound should be further evaluated for antineoplastic properties. Preferably, the $IC_{50}$ value for the novel PDE inhibition should be less than 50 µM for the compound to be further considered for potential use.

F. Determining Whether A Compound Reduces Tumor Cell Growth

In an alternate embodiment, the method of the present invention involves further determining whether the compound reduces the growth of tumor cells. Various cell lines can be used in the sample depending on the tissue to be tested. For example, these cell lines include: SW-480—colonic adenocarcinoma; HT-29—colonic adenocarcinoma, A-427—lung adenocarcinoma carcinoma; MCF-7—breast adenocarcinoma; and UACC-375—melanoma line; and DU145—prostrate carcinoma. Cytotoxicity data obtained using these cell lines are indicative of an inhibitory effect on neoplastic lesions. These cell lines are well characterized, and are used by the United States National Cancer Institute in their screening program for new anti-cancer drugs.

A compound's ability to inhibit tumor cell growth can be measured using the HT-29 human colon carcinoma cell line obtained from ATCC. HT-29 cells have previously been characterized as a relevant colon tumor cell culture model (Fogh, J., and Trempe, G. *In. Human Tumor Cells in Vitro,* J. Fogh (eds.), Plenum Press, New York, pp. 115–159, 1975). HT-29 cells are maintained in RPMI media supplemented with 5% fetal bovine calf serum (Gemini Bioproducts, Inc., Carlsbad, Calif.) and 2 mm glutamine, and 1% antibiotic-antimycotic in a humidified atmosphere of 95% air and 5% $CO_2$ at 37° C. Briefly, HT-29 cells are plated at a density of 500 cells/well in 96 well microtiter plates and incubated for 24 hours at 37° C. prior to the addition of compound. Each determination of cell number involved six replicates. After six days in culture, the cells are fixed by the addition of cold trichloroacetic acid to a final concentration of 10% and protein levels are measured using the sulforhodamine B (SRB) calorimetric protein stain assay as previously described by Skehan, P., Storeng, R., Scudiero, D., Monks, A., McMahon, J., Vistica, D., Warren, J. T., Bokesch, H., Kenney, S., and Boyd, M. R., "New Colorimetric Assay For Anticancer-Drug Screening," *J. Natl. Cancer Inst.* 82: 1107–1112, 1990, which is incorporated herein by reference.

In addition to the SRB assay, a number of other methods are available to measure growth inhibition and could be substituted for the SRB assay. These methods include counting viable cells following trypan blue staining, labeling cells capable of DNA synthesis with BrdU or radiolabeled thymidine, neutral red staining of viable cells, or MTT staining of viable cells.

Significant tumor cell growth inhibition greater than about 50% at a dose of 100 µM or below is further indicative that the compound is useful for treating neoplastic lesions. Preferably, an $IC_{50}$ value is determined and used for comparative purposes. This value is the concentration of drug needed to inhibit tumor cell growth by 50% relative to the control. Preferably, the $IC_{50}$ value should be less than 100 $\mu$M for the compound to be considered further for potential use for treating neoplastic lesions.

G. Determining Whether A Compound Induces Apoptosis

In a second alternate embodiment, the screening method of the present invention further involves determining whether the compound induces apoptosis in cultures of tumor cells.

Two distinct forms of cell death may be described by morphological and biochemical criteria: necrosis and apoptosis. Necrosis is accompanied by increased permeability of the plasma membrane; the cells swell and the plasma membrane ruptures within minutes. Apoptosis is characterized by membrane blebbing, condensation of cytoplasm and the activation of endogenous endonucleases.

Apoptosis occurs naturally during normal tissue turnover and during embryonic development of organs and limbs. Apoptosis also is induced by cytotoxic T-lymphocytes and natural killer cells, by ionizing radiation and by certain chemotherapeutic drugs. Inappropriate regulation of apoptosis is thought to play an important role in many pathological conditions including cancer, AIDS, or Alzheimer's disease, etc. Compounds can be screened for induction of apoptosis using cultures of tumor cells maintained under conditions as described above. Treatment of cells with test compounds involves either pre- or post-confluent cultures and treatment for two to seven days at various concentrations. Apoptotic cells are measured in both the attached and "floating" compartments of the cultures. Both compartments are collected by removing the supernatant, trypsinizing the attached cells, and combining both preparations following a centrifugation wash step (10 minutes, 2000 rpm). The protocol for treating tumor cell cultures with sulindac and related compounds to obtain a significant amount of apoptosis has been described in the literature. (See, Piazza, G. A., et al., *Cancer Research,* 55:31 10–16, 1995, which is incorporated herein by reference). The novel features include collecting both floating and attached cells, identification of the optimal treatment times and dose range for observing apoptosis, and identification of optimal cell culture conditions.

Following treatment with a compound, cultures can be assayed for apoptosis and necrosis by florescent microscopy following labeling with acridine orange and ethidium bromide. The method for measuring apoptotic cell number has previously been described by Duke & Cohen, "Morphological And Biochemical Assays Of Apoptosis," *Current Protocols In Immunology,* Coligan et al., eds., 3.17.1–3.17.16 (1992, which is incorporated herein by reference).

For example, floating and attached cells can be collected by trypsinization and washed three times in PBS. Aliquots of cells can be centrifuged. The pellet can then be re-suspended in media and a dye mixture containing acridine orange and ethidium bromide prepared in PBS and mixed gently. The mixture can then be placed on a microscope slide and examined for morphological features of apoptosis.

Apoptosis can also be quantified by measuring an increase in DNA fragmentation in cells that have been treated with test compounds. Commercial photometric EIA for the quantitative, in vitro determination of cytoplasmic histone-associated-DNA-fragments (mono- and oligonucleosomes) are available (Cell Death Detection ELISA$^{okys}$, Cat. No. 1,774,425, Boehringer Mannheim). The Boehringer Mannheim assay is based on a sandwich-enzyme-immunoassay principle using mouse monoclonal antibodies directed against DNA and histones, respectively. This allows the specific determination of mono- and oligonucleosomes in the cytoplasmatic fraction of cell lysates.

According to the vendor, apoptosis is measured in the following fashion. The sample (cell-lysate) is placed into a streptavidin-coated microtiter plate ("MTP"). Subsequently, a mixture of anti-histone-biotin and anti-DNA peroxidase conjugate are added and incubated for two hours. During the incubation period, the anti-histone antibody binds to the histone-component of the nucleosomes and simultaneously fixes the immunocomplex to the streptavidin-coated MTP via its biotinylation. Additionally, the anti-DNA peroxidase antibody reacts with the DNA component of the nucleosomes. After removal of unbound antibodies by a washing step, the amount of nucleosomes is quantified by the peroxidase retained in the immunocomplex. Peroxidase is determined photometrically with ABTS7 (2,2'-Azido-[3-ethylbenzthiazolin-sulfonate]) as substrate.

For example, SW-480 colon adenocarcinoma cells are plated in a 96-well MTP at a density of 10,000 cells per well. Cells are then treated with test compound, and allowed to incubate for 48 hours at 37° C. After the incubation, the MTP is centrifuged, and the supernatant is removed. The cell pellet in each well is then resuspended in lysis buffer for 30 minutes. The lysates are then centrifuged and aliquots of the supernatant (i.e., the cytoplasmic fraction) are transferred into a streptavidin-coated MTP. Care is taken not to shake the lysed pellets (i.e. cell nucleii containing high molecular weight, unfragmented DNA) in the MTP. Samples are then analyzed.

Fold stimulation ($FS=OD_{max}/OD_{veh}$), an indicator of apoptotic response, is determined for each compound tested at a given concentration. $EC_{50}$ values may also be determined by evaluating a series of concentrations of the test compound.

Statistically significant increases in apoptosis (i.e., greater than 2 fold stimulation at a concentration of 100 $\mu$M) are further indicative that the compound is useful for treating neoplastic lesions. Preferably, the $EC_{50}$ value for apoptotic activity should be less than 100 $\mu$M for the compound to be further considered for potential use for treating neoplastic lesions. $EC_{50}$ is herein defined as the concentration that causes 50% induction of apoptosis relative to vehicle treatment.

II. Mammary Gland Organ Culture Model Tests

Test compounds identified by the above methods can be tested for antineoplastic activity by their ability to inhibit the incidence of pre-neoplastic lesions in a mammary gland organ culture system. This mouse mammary gland organ culture technique has been successfully used by other investigators to study the effects of known antineoplastic agents such as certain NSAIDs, retinoids, tamoxifen, selenium, and certain natural products, and is useful for validation of the screening method of the present invention.

For example, female BALB/c mice can be treated with a combination of estradiol and progesterone daily, in order to prime the glands to be responsive to hormones in vitro. The animals are sacrificed, and thoracic mammary glands are excised aseptically and incubated for ten days in growth media supplemented with insulin, prolactin, hydrocortisone, and aldosterone. DMBA (7,12-dimethylbenz(a)anthracene) is added to medium to induce the formation of premalignant lesions. Fully developed glands are then deprived of prolactin, hydrocortisone, and aldosterone, resulting in the regression of the glands but not the pre-malignant lesions.

The test compound is dissolved in DMSO and added to the culture media for the duration of the culture period. At the end of the culture period, the glands are fixed in 10% formalin, stained with alum carmine, and mounted on glass slides. The incidence of forming mammary lesions is the ratio of the glands with mammary lesions to glands without lesions. The incidence of mammary lesions in test compound treated glands is compared with that of the untreated glands.

The extent of the area occupied by the mammary lesions can be quantitated by projecting an image of the gland onto a digitation pad. The area covered by the gland is traced on the pad and considered as 100% of the area. The space covered by each of the non-regressed structures is also outlined on the digitization pad and quantitated by the computer.

III. Anti-Neoplastic Pharmaceutical Compositions Containing cGMP PDE Inhibitor/JNK1 Activator Compounds As explained above, exisulind is one compound that exhibits desirable anti-neoplastic properties. Its efficacy and use as an anti-neoplastic was discovered before it was understood that the compound acted by inhibiting cGMP-specific PDE activity and activating JNK1 in neoplastic cells.

Among other things, the verification that the selection process of this invention could be used to select compounds for human treatment was obtained in human clinical trials in patients with neoplasias. By understanding after the fact that exisulind was anti-neoplastic (in vitro), that it had the profile of a desirable compound meeting the selection criterion of this invention, the success of the compound in two human clinical trials establishes that other compounds can be selected meeting the selection criterion of this invention.

As indicated above, a number of neoplasias harbor the APC mutation. Among other things, the verification of the selection process of this invention was established in human clinical trials in patients with neoplasia harboring the APC mutation.

The APC mutation was first discovered in patients with the hereditary neoplasia, adenomatous polyposis coli ("APC"). The APC disease is characterized by the appearance in the teen years of hundreds to thousands of polyps in the colon, and the common therapy is surgical removal of the colon before the age of 20.

The first clinical trial involved patients with APC using exisulind. In that study, each patient had already had his/her colon removed, except for a small section of colon adjacent the rectum (where the small intestine was attached) to preserve rectal function. However, such a patient commonly forms polyps in the small remaining colonic section, which polyps require periodic removal (e.g., by electrocautery).

That trial where exisulind was selected was a prevention trial designed to evaluate the anti-neoplastic characteristics of the drug by comparing the cumulative number of new polyps formed over twelve months by the drug and placebo groups. Eligible patients were those who form between 9 and 44 polyps per year. Patients were fully ablated (had all polyps removed) at the start of the study, at the end of 6 months and at the end of 12 months. The study enrolled thirty-four eligible patients. Based on the estimated mean number of polyps formed over a year in APC patients who had historically produced 9 to 44 polyps per year, exisulind was clinically and statistically significantly better than placebo in decreasing the rate of polyp formation. Based on the median number of polyps produced in the first six months of the study, patients treated with exisulind developed approximately one-third the number of polyps as patients treated with placebo (median values 9 polyps/year and 26 polyps/year, respectively; p=0.013). Based on the median number of polyps produced over the entire 12 months of the study, patients treated with exisulind produced approximately half the number of polyps as patients treated with placebo (median values 18 polyps/year and 38 polyps/year, respectively; p=0.020).

A separate clinical trial was also performed on male patients who had prostate cancer, and as a result had their prostates removed. The study was conducted in patients with detectable PSA (prostate specific antigen) levels that were rising following radical prostatectomy, indicating recurrence of prostate cancer.

96 patients were enrolled in the prostate cancer evaluation: a double-blind, placebo-controlled, multi-center trial involving exisulind administered to the drug-receiving patients at 500 mg/day. As presented below, the data show a statistically significant difference in PSA levels between the. exisulind-treated group and the placebo-treated group. PSA levels in the exisulind-treated group were significantly reduced as compared with the PSA levels of the placebo-treated group. Although a rising level of PSA is not itself a disease condition, it is widely regarded in the medical community as a surrogate marker indicative of the presence of recurrence of prostate cancer in such men.

In addition to performing an evaluation based on the differences in mean PSA levels between the exisulind and placebo groups as a whole, the interim analysis included subgroup analysis. The patients in the study were classified into high, intermediate and low risk groups in terms of their risk of developing metastatic disease. This classification was performed using the methodology published in the *Journal of the American Medical Association* (*JAMA* May 5, 1999, pp. 1591–97). To ascertain which study patients fell into which risk group, medical histories were supplied to a researcher who was blinded as to whether patients were on drug or placebo; he assigned study patients to the appropriate risk groups according to the above referenced published methodology. The statistical analysis revealed statistically significant differences in mean PSA levels between exisulind and placebo patients in both high and intermediate risk groups.

The data from the prostate study are as follows:

TABLE 1

Effect of Exisulind On Mean PSA Level
In Men Post-Prostatectomy With Rising PSA

| Group | Placebo | Exisulind | "p" value |
| --- | --- | --- | --- |
| Overall | 4.49 | 2.85 | 0.0004 |
| High Risk | 4.98 | 2.91 | 0.0002 |
| Intermediate Risk | 6.24 | 2.95 | 0.0053 |

In these exisulind trials and several others involving the drug in other indications, safety was evaluated by monitoring adverse events (AEs), clinical laboratory tests (hematology, serum chemistry, and urinalysis), vital signs (blood pressure, pulse rate, respiratory rate, temperature, and weight), physical examination, and upper endoscopy.

No outstanding safety issues have been demonstrated in the clinical trials conducted with exisulind to date in over 400 patients. Exisulind did not demonstrate any blood dyscrasia, dose-limiting vomiting, or neurological or renal toxicities associated with convention chemotherapeutics. It also did not cause any clinically significant changes in vital signs. In fact, in paired biopsies of polyp and normal colonic tissues in APC patients, it was found that exisulind increased apoptosis rates in polyp, but not normal colonic tissues, suggesting minimal effects on normal tissues.

At doses above the maximum tolerated dose (MTD=600 mg in patients with subtotal colectomy; 400 mg in patients with intact colons; 350 mg in pediatric patients), the only dose-limiting adverse events found were elevations in liver function tests (LFTs) that are seen early during treatment. When experienced, LFT elevations were rapidly reversible, and do not recur when the dose has been lowered.

Other events (e.g., occasional abdominal pain) were typically short lasting and of mild to moderate intensity, and did not necessitate discontinuing or lowering of the exisulind dose.

In short, these trials demonstrated that exisulind is an effective, well-tolerated chronic therapy for the clinical management of neoplasia. Thus, these results illustrate that selecting an additional compound that inter alia inhibits cGMP-specific PDE activity (as well as meeting the other selection criteria of this invention) can result in a therapeutically effective drug, in vivo.

A second drug that was also invented before its mechanism of action was found to involve cGMP inhibition and before it was known to meet the selection criterion of this invention is Compound B. It has been demonstrated in in vitro and in vivo evaluations as anti-neoplastic having activities against a broad range of neoplasias. It is also safe in animal studies and in a single, escalating dose human study.

As one skilled in the art will recognize from the data presented below, Compound B can safely be given to animals at doses far beyond the tolerable (and in many cases toxic) doses of conventional chemotherapeutics or anti-neoplastic NSAIDs. For example, in an acute toxicity study in rats, single oral doses of Compound B administered (in a 0.5% carboxy-methylcellulose vehicle) at doses up to and including 2000 mg/kg resulted in no observable signs of toxicity. At 4000 mg/kg, body weight gains were slightly reduced. A single dose of 1000 mg/kg administered intraperitoneally resulted in reduced body weight gain, with mesenteric adhesions seen in some animals from this group at necropsy.

In dogs, the administration of Compound B in capsules at 1000 mg/kg resulted in no signs of toxicity to the single group of two male and two female dogs. Due to the nature of Compound B capsules, this dose necessitated the use of at least 13 capsules to each animal, which was judged to be the maximum number without subjecting the animals to stress. Therefore, these dogs were subsequently administered seven consecutive doses of 1000 mg/kg/day. At no time in either dosing phase were any obvious signs of drug-related effects observed.

Thus, on a single-dose basis, Compound B is not acutely toxic. Based on the findings of these studies, the oral $LD_{50}$ of Compound B was considered to be greater than 1000 mg/kg in dogs and 4000 mg/kg in rats, and the intraperitoneal $LD_{50}$ was considered to be greater than 1000 mg/kg in rats.

A seven-day dose-range finding study in rats, where Compound B was evaluated by administering it at doses of 0, 50, 500 or 2000 mg/kg/day resulting in no observable signs of toxicity at 50 mg/kg/day. At 500 mg/kg/day, treatment-related effects were limited to an increase in absolute and relative liver weights in female rats. At 2000 mg/kg/day, effects included labored breathing and/or abnormal respiratory sounds, decreased weights gains and food consumption in male rats, and increased liver weights in female rats. No hematological or blood chemistry changes nor any microscopic pathology changes, were seen at any dose level.

A 28-day study in rats was also carried out at 0, 50, 500 and 2000 mg/kg/day. There were no abnormal clinical observations attributed to Compound B, and body weight changes, ophthalmoscopic examinations, hematological and blood chemistry values and urinalysis examinations were unremarkable. No macroscopic tissue changes were seen at necropsy. Organ weight data revealed statistically significant increase in liver weights at 2000 mg/kg/day, and statistically significant increases in thyroid weights for the 2000 mg/kg/day group. The slight increases at the lower doses were not statistically significant. Histopathological evaluation of tissues indicated the presence of traces of follicular cell hypertrophy, increased numbers of mitotic figures (suggestive of possible cell proliferation) in the thyroid gland and mild centrilobular hypertrophy in the liver. These changes were generally limited to a small number of animals at the 2000 mg/kg/day dose, although one female at 500 mg/kg/day had increased mitotic figures in the thyroid gland. The findings in the liver may be indicative of a very mild stimulation of microsomal enzymes, resulting in increased metabolism of thyroid hormones, which in turn resulted in thyroid stimulation. Thus, one skilled in the art will recognize that these effects are extremely minimal compared to what one would expect at similar doses of conventional chemotherapeutics or NSAIDs.

To further establish the safety profile of Compound B, a study was performed to evaluate whether Compound B-induced apoptosis of prostate tumor cell lines was comparable to its effects on prostate epithelial cells derived from normal tissue. The androgen-sensitive prostate tumor cell line, LNCaP (from ATCC (Rockville, Md.)) was propagated under standard conditions using RPMI 160 medium containing 5% fetal calve serum and 2 mM glutamine. Primary prostate epithelial cell cultures (PrEC) derived from normal prostate (from Clonetics Inc. (San Diego, Calif.)) were grown under the same conditions as the tumor cell line except a serum-free medium optimized for the growth of such cultures was used (Clonetics Inc). For the experiments, LNCaP or PrEC cells were seeded in 96 well plates at a density of 10,000 cells per well. After 24 hours, the cells were treated with either vehicle (0.1% DMSO) or 50 $\mu$M Compound B (free base) solubilized in DMSO. After various drug treatment times (4, 24, 48, 72, or 99 hours) the cells were lysed and processed for measurement of histone-associated DNA as an indicator of apoptotic cell death (see, Piazza et al., *Cancer Research* 57: 2452–2459, 1997).

Figure 6:
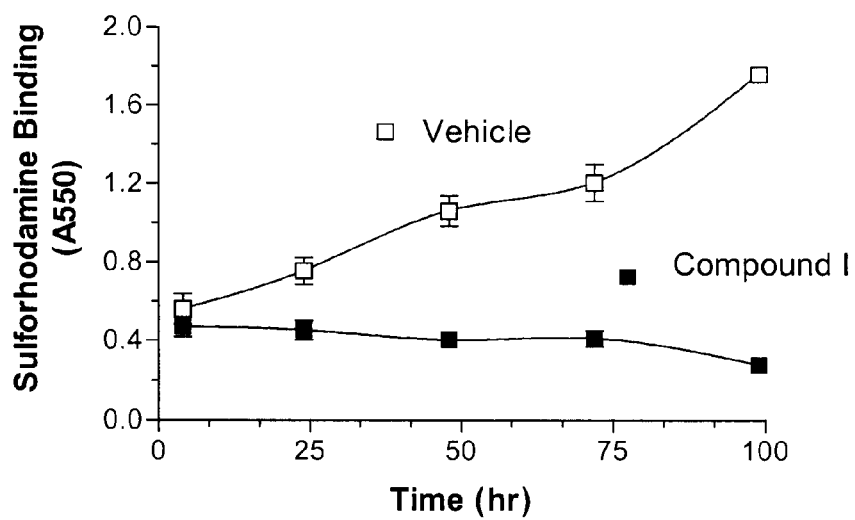
FIG. 6 shows a time-dependent increase in the amount of histone-associated fragmented DNA in LNCaP cell cultures following treatment with 50 $\mu$M Compound I.

FIG. 6 shows a time-dependent increase in the amount of histone-associated fragmented DNA in LNCaP cell cultures following treatment with 50 $\mu$M Compound B (free base). A significant increase in fragmented DNA was detected after 24 hours of treatment, and the induction was sustained for up to 4 days of continuous treatment. By contrast, treatment of PrEC ("normal" prostate) cells with Compound B (50 $\mu$M) did not affect DNA fragmentation for up to 4 days of treatment. These results demonstrate a selective induction of apoptosis in neoplastic cells, as opposed to normal cells. This is in marked contrast to conventional chemotherapeutics that induce apoptosis or necrosis in rapidly growing normal and neoplastic cells alike.

Finally as to safety, in a single, escalating dose human clinical trial, patients, human safety study in which the drug was taken orally, Compound B produced no significant side effects at any dose, including doses above the level predicted to be necessary to produce anti-cancer effects.

As indicated above, Compound B also exhibits potent anti-neoplastic properties. The growth inhibition $IC_{50}$ value obtained for Compound B was 0.7 $\mu$M in the SW-480 cell line. This result has been confirmed by evaluating Compound B in rodents using aberrant crypt foci ("ACF") as an indicator of carcinogenesis (see, Bird, Cancer Lett. 37: 147–151, 1987). This established rodent model of azoxymethane ("AOM")-induced carcinogenesis was used to assess the effects of Compound B (free base and salt) on colon cancer development in vivo. ACF are precursors to colonic tumors, and ACF inhibition is predictive of chemopreventive efficacy.

In the rats in this experiment, ACF initiation was achieved by two consecutive weekly injections of the carcinogen. Compound B was administered one week prior to ACF initiation and for the duration of the experiment. ACFs were scored after 5 weeks of treatment. Compound B was administered orally to male Fisher 344 rats in the rat chow. Daily food consumption (mg/kg body weight) varied over the course of the study, and therefore Compound B dose was expressed a grams per kg of diet to provide a basis of comparison between doses. To determine if Compound B had an adverse effect on growth and/or feeding behavior, body weight was determined throughout the course of the experiment. The experimental groups gained less weight than the controls, which was indicative of bioavailability. However, the weight differences were less than 10% and not considered to affect ACF formation.

The free base of Compound B inhibited ACF formation as measured by a reduction of crypts per colon. The data are summarized in Table 2. With the exception of the low dose group (only 0.5 g/kg diet), the differences between treatment and control groups were substantial, and statistically significant in the case of the 1.0 and 2.0 g/kg diet group.

TABLE 2

Inhibition of Aberrant Crypt Foci by Compound B

| Compound Dose (g/kg diet) | n | Mean ACF/colon (+SE) | % Control | p (t-test) vs. control |
|---|---|---|---|---|
| Control | 10 | 149 ± 9 | — | — |
| 0.5 | 7 | 149 ± 14 | 100 | 0.992 |
| 1 | 10 | 111 ± 9 | 75 | 0.008 |
| 1.5 | 10 | 132 ± 4 | 89 | 0.101 |
| 2.0 | 10 | 107 ± 15 | 72 | 0.029 |

Also, Compound B retrospectively met the selection criterion of this invention, and was one of the compounds used to establish the validity of this selection criteria. For example, using the protocols described previously, Compound B has a cGMP-specific PDE $IC_{50}$ value of 0.68 $\mu$M utilizing cGMP-specific PDE from HT29 cell extracts. Its COX I inhibition (at 100 $\mu$M) was less than 25%.

As for being pro-apoptotic, Compound B's DNA fragmentation $EC_{50}$ was 15 $\mu$M. In addition, the percent apoptosis for Compound B in SW-480 is shown in Table 3 at various drug concentrations.

TABLE 3

Apoptosis Induction of HT-29 Cells of SW-480 Colon Adenocarcinoma Cells by Compound B as Determined by Morphology

| Treatment | Dose | % Apoptosis |
|---|---|---|
| Vehicle (0.1% DMSO) | — | 1 |
| Compound B | 0.35 $\mu$M | 16 |
| Compound B | 0.7 $\mu$M | 27 |
| Compound B | 1.5 $\mu$M | 88 |

Compound B's activity is not confined to activity against colon cancer cell lines or animal models of colon cancer. It has a broad range of anti-neoplastic effects in various neoplastic cell lines. Various types of human cancer cell lines were propagated under sterile conditions in RPMI 1640 medium with 10% fetal bovine serum, 2 mM L-glutamine and sodium bicarbonate. To determine growth inhibitory effects of Compound B, cells were seeded in 96-well plates at a density of 1000 cells per well. Twenty-four hours after plating, the cells were dosed with various concentrations of the free base of Compound B solubilized in DMSO (final concentration 0.1%). The effect of the drug on tumor cell growth was determined using the neutral red cytotoxicity assay following five days of continuous treatment. Neutral red is a dye that is selectively taken up by viable cells by an ATP-dependent transport mechanism.

As summarized in Table 4, Compound B (free base) displayed potent growth inhibitory activity when evaluated against a panel of cultured human cell lines derived from various tissue origins. Compound B displayed comparable growth inhibitory effects regardless of the histogenesis of the tumor from which the cell lines were derived. The $GI_{50}$ value (concentration of drug to inhibit growth by 50% relative to vehicle control) calculated for all cell lines was 1–2 $\mu$M.

In addition to the data in the table below, we observed comparable sensitivity of human leukemia cell lines (CCRF-CEM, K562, and Molt-4), a myeloma cell line (RPMI8226), a pancreatic tumor cell line (PAN-1), and an ovarian tumor cell line (OVCAR-3) to Compound B (HCl salt).

TABLE 4

Growth Inhibition of Various Human Tumor Cell Lines by Compound B

| Cell Line | Tumor origin | $GI_{50} \mu M$ | $GI_{90} \mu M$ |
|---|---|---|---|
| Colo 205 | Colon | 1.6 | 2.4 |
| HCT-15 | Colon | 1.7 | 3.0 |
| HT-29 | Colon | 2.1 | 8.0 |
| SW-620 | Colon | 1.7 | 2.5 |
| DU145 | Prostate | 1.6 | 2.8 |
| PC-3 | Prostate | 1.7 | 82.5 |
| NCI-H23 | Lung | 1.7 | 2.5 |
| NCI-H322M | Lung | 2.1 | 13.2 |
| NCI-H460 | Lung | 1.9 | 30.0 |
| NCI-H82 | Lung | 1.7 | 5.8 |
| MDA-MB-231 | Breast | 1.8 | 77.6 |
| MDA-MB-435 | Breast | 1.6 | 2.3 |
| UISO-BCA-1 | Breast | 1.5 | 4.7 |
| Molt-4* | Leukemia | 1.6 | ND |
| CCRF-CEM* | Leukemia | 1.4 | ND |
| K-562* | Leukemia | 1.8 | ND |
| RPMI-8226* | Myeloma | 1.2 | ND |
| OVCAR* | Ovary | 1.2 | ND |
| PANC-1* | Pancreas | 2.2 | ND |

*Testing was done with the free base of the compound unless otherwise indicated with an asterisk in which case testing was done with the HCl salt.

Given the animal and human safety characteristics, and the animal and very broad cell culture efficacy of Compound B, it is clear that compounds meeting the selection criteria of this invention (including cGMP-specific PDE inhibition) can are useful anti-neoplastic therapeutics.

As to identifying structurally additional cGMP-specific PDE inhibiting compounds that can be effective therapeutically as anti-neoplastics, one skilled in the art has a number of useful model compounds disclosed herein (as well as their analogs incorporated by reference) that can be used as the bases for computer modeling of additional compounds having the same conformations but different chemically. For example, software such as that sold by Molecular Simulations Inc. release of WebLab® ViewerPro™ includes molecular visualization and chemical communication capabilities. Such software includes functionality, including 3D visualization of known active compounds to validate sketched or imported chemical structures for accuracy. In addition, the software allows structures to be superimposed based on user-defined features, and the user can measure distances, angles, or dihedrals.

In this situation, since the structures of other active compounds are disclosed above, one can apply cluster analysis and 2D and 3D similarity search techniques with such software to identify potential new additional compounds that can then be screened and selected according to the selection criteria of this invention. These software methods rely upon the principle that compounds, which look alike or have similar properties, are more likely to have similar activity, which can be confirmed using the selection criterion of this invention.

Likewise, when such additional compounds are computer modeled, many such compounds and variants thereof can be synthesized using known combinatorial chemistry techniques that are commonly used by those of ordinary skill in the pharmaceutical industry. Examples of a few for-hire combinatorial chemistry services include those offered by New Chemical Entities, Inc. of Bothell Wash., Protogene Laboratories, inc., of Palo Alto, Calif., Axys, Inc. of South San Francisco, Calif., Nanosyn, Inc. of Tucson, Ariz., Trega, Inc. of San Diego, Calif., and RBI, Inc. of Natick, Mass. There are a number of other for-hire companies. A number of large pharmaceutical companies have similar, if not superior, in-house capabilities. In short, one skilled in the art can readily produce many compounds for screening from which to select promising compounds for treatment of neoplasia having the attributes of compounds disclosed herein.

To further assist in identifying compounds that can be screened and then selected using the criterion of this invention, knowing the binding of selected anti-neoplastic compounds to PDE5 protein is of interest. By the procedures discussed below, it was found that preferable, desirable compounds meeting the selection criteria of this invention bind to the cGMP catalytic region of PDE5.

To establish this, a PDE5 sequence that does not include the catalytic domain was used. One way to produce such a sequence is to express that sequence as a fusion protein, preferably with glutiathione S-transferase ("GST"), for reasons that will become apparent.

RT-PCR method is used to obtain the cGB domain of PDE5 with forward and reverse primers designed from bovine PDE5A cDNA sequence (McAllister-Lucas L. M. et al, *J. Biol. Chem.* 268, 22863–22873, 1993) and the selection among PDE 1–10 families. 5'-3', Inc. kits for total RNA followed by oligo (dT) column purification of mRNA are used with HT-29 cells. Forward primer (GAA-TTC-TGT-TAG-AAA-AGC-CAC-CAG-AGA-AAT-G, 203–227) and reverse primer (CTC-GAG-CTC-TCT-TGT-TTC-TTC-CTC-TGC-TG, 1664–1686) are used to synthesize the 1484 bp fragment coding for the phosphorylation site and both low and high affinity cGMP binding sites of human PDE5A (203–1686 bp, cGB-PDE5). The synthesized cGB-PDE5 nucleotide fragment codes for 494 amino acids with 97% similarity to bovine PDE5A. It is then cloned into pGEX-5X-3 glutathione-S-transferase (GST) fusion vector (Pharnacia Biotech )with tac promoter, and EcoRI and XhoI cut sites. The fusion vector is then transfected into *E. Coli* BL21 (DE3) bacteria (Invitrogen). The transfected BL21 bacteria is grown to log phase, and then IPTG is added as an inducer. The induction is carried at 20° C. for 24 hrs. The bacteria are harvested and lysed. The soluble cell lysate is incubated with GSH conjugated Sepharose 4B (GSH-Sepharose 4B). The GST-cGB-PDE5 fusion protein can bind to the GSH-Sepharose beads, and the other proteins are washed off from beads with excessive cold PBS.

The expressed GST-cGB-PDE5 fusion protein is displayed on 7.5% SDS-PAGE gel as an 85 Kd protein. It is characterized by its cGMP binding and phosphorylation by protein kinases G and A. It displays two cGMP binding sites, and the $K_d$ is 1.6±0.2 $\mu$M, which is close to $K_d$=1.3 $\mu$M of the native bovine PDE5. The GST-cGB-PDE5 on GSH-conjugated sepharose beads can be phosphorylated in vitro by cGMP-dependent protein kinase and cAMP-dependent protein kinase A. The $K_m$ of GST-cGB-PDE5 phosphorylation by PKG is 2.7 $\mu$M and Vmax is 2.8 $\mu$M, while the $K_m$ of BPDEtide phosphorylation is 68 $\mu$M. The phosphorylation by PKG shows molecular phosphate incorporated into GST-cGB-PDE5 protein on a one-to-one ratio.

A cGMP binding assay for compounds of interest (Francis S. H. et al, J. Biol. Chem. 255, 620–626, 1980) is done in a total volume of 100 $\mu$L containing 5 mM sodium phosphate buffer (pH=6.8), 1 mM EDTA, 0.25 mg/mL BSA, $H^3$-cGMP (2 $\mu$M, NEN) and the GST-cGB-PDE5 fusion protein (30 $\mu$g/assay). Each compound to be tested is added at the same time as $^3$H-cGMP substrate, and the mixture is incubated at 22° C. for 1 hour. Then, the mixture is transferred to Brandel MB-24 cell harvester with GF/B as the filter membrane followed by 2 washes with 10 mL of cold 5 mM potassium buffer( pH 6.8). The membranes are then cut out and transferred to scintillation vials followed by the addition of 1 mL of $H_2O$ and 6 mL of Ready Safe™ liquid scintillation cocktail to each vial. The vials are counted on a Beckman LS 6500 scintillation counter.

For calculation, blank samples are prepared by boiling the binding protein for 5 minutes, and the binding counts are <1% when compare to unboiled protein. The quenching by filter membrane or other debris are also calibrated.

Figure 7:
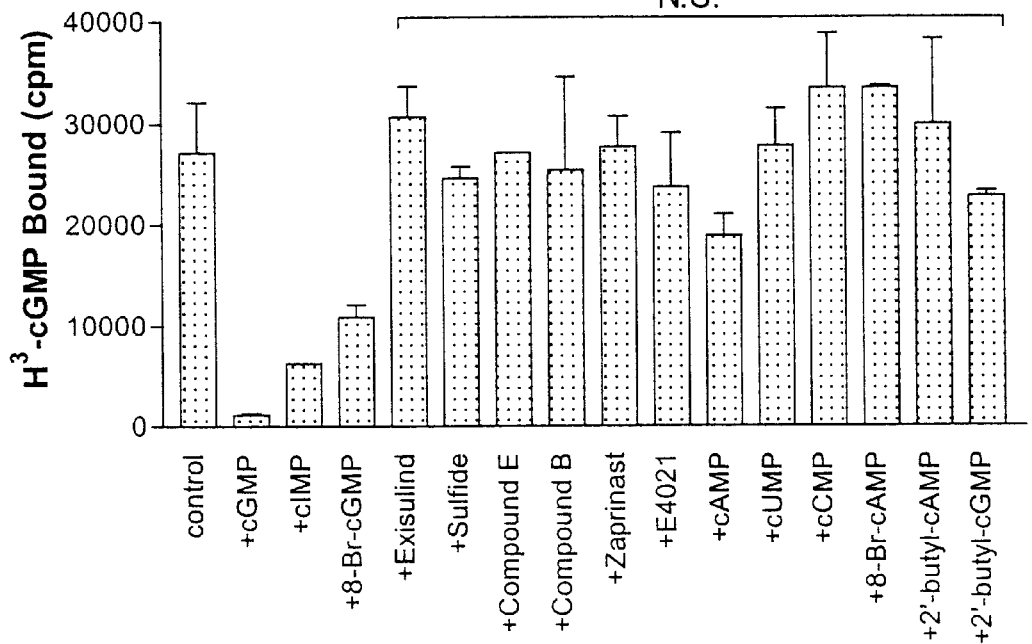
FIG. 7 is a bar graph illustrating the specific binding of the non-catalytic cGMP binding sites of PDE5 for cyclic nucleotide analogs and selected PDE5 inhibitors.

PDE5 inhibitors, sulfide, exisulind, Compound B, Compound A, E4021 and zaprinast, and cyclic nucleotide analogs, cAMP, cyclic IMP, 8-bromo-cGMP, cyclic UMP, cyclic CMP, 8-bromo-cAMP, 2'-O-butyl-cGMP and 2'-O-butyl-cAMP are selected to test whether they could competitively bind to the cGMP binding sites of the GST-cGB-PDE5 protein. The results were shown in FIG. 7. cGMP specifically binds GST-cGB-PDE5 protein. Cyclic AMP, cUMP, cCMP, 8-bromo-cAMP, 2'-O-butyl-cAMP and 2'-O-butyl-cGMP did not compete with cGMP in binding. Cyclic IMP and 8-bromo-cGMP at high concentration (100 $\mu$M) can partially compete with cGMP (2 $\mu$M) binding. None of the PDE5 inhibitors showed any competition with cGMP in binding of GST-cGB-PDE5. Therefore, they do not bind to the cGMP binding sites of PDE5.

However, Compound A does competitively (with cGMP) bind to PDE 5 (i.e., peak A). (Compound A also competitively (with cGMP) binds to PDE peak B.). Given that Compound A does not bind to the cGMP-binding site of PDE5, and the fact that there is competitive binding between Compound A and cGMP at all, mean that desirable compounds such as Compound A bind to the cGMP catalyic site on PDE5, information that is readily obtainable by one skilled in the art (with conventional competitive binding experiments) but which can assist one skilled in the art more readily to model other compounds. Thus, with the chemical structures of desirable compounds presented herein and the cGMP binding site information, one skilled in the art can model, identify and select (using the selection criteria of this invention) other chemical compounds for use as therapeutics.

Compounds selected in accordance with the methodology of this invention may be formulated into pharmaceutical compositions as is well understood from the ordinary meaning of the term "pharmaceutical composition" i.e., a compound (e.g., like the solids described above) and a pharmaceutically acceptable carrier for delivery to a patient by oral administration in solid or liquid form, by IV or IP administration in liquid form, by topical administration in ointment form, or by rectal or topical administration in a suppository formulation. Carriers for oral administration are most preferred.

As is well known in the art pharmaceutically acceptable carriers in pharmaceutical compositions for oral administration include capsules, tablets, pills, powders, troches and granules. In such solid dosage forms, the carrier can comprise at least one inert diluent such as sucrose, lactose or starch. Such carriers can also comprise, as is normal practice, additional substances other than diluents, e.g., lubricating agents such as magnesium stearate. In the case of capsules, tablets, troches and pills, the carriers may also comprise buffering agents. Carriers such as tablets, pills and granules can be prepared with enteric coatings on the surfaces of the tablets, pills or granules. Alternatively, the enterically-coated compound can be pressed into a tablet, pill, or granule, and the tablet, pill or granules for administration to the patient. Preferred enteric coatings include those that dissolve or disintegrate at colonic pH such as shellac or Eudraget S.

Pharmaceutically acceptable carriers in pharmaceutical compositions include liquid dosage forms for oral administration, e.g., pharmaceutically acceptable emulsions, solutions, suspensions, syrups and elixirs containing inert diluents commonly used in the art, such as water. Besides such inert diluents, compositions can also include adjuvants such as wetting agents, emulsifying and suspending agents, and sweetening, flavoring and perfuming agents.

Pharmaceutically acceptable carriers in pharmaceutical compositions for IV or IP administration include common pharmaceutical saline solutions.

Pharmaceutically acceptable carriers in pharmaceutical compositions for topical administration include DMSO, alcohol or propylene glycol and the like that can be employed with patches or other liquid-retaining material to hold the medicament in place on the skin so that the medicament will not dry out.

Pharmaceutically acceptable carriers in pharmaceutical compositions for rectal administration are preferably suppositories that may contain, in addition to the compounds of this invention excipients such as cocoa butter or a suppository wax, or gel.

A pharmaceutically acceptable carrier and compounds of this invention are formulated into pharmaceutical compositions in unit dosage forms for administration to a patient. The dosage levels of active ingredient (i.e., compounds selected in accordance with this invention) in the unit dosage may be varied so as to obtain an amount of active ingredient effective to achieve neoplasia-eliminating activity in accordance with the desired method of administration (i.e., oral or rectal). The selected dosage level therefore depends upon the nature of the active compound administered (e.g., its $IC_{50}$, which can be readily ascertained), the route of administration, the desired duration of treatment, and other factors. If desired, the unit dosage may be such that the daily requirement for active compound is in one dose, or divided among multiple doses for administration, e.g., two to four times per day. For IV administration, an initial dose for administration can be ascertained by basing it on the dose that achieves the $IC_{50}$ in the plasma contents of the average adult male (i.e., about 4 liters). Initial doses of active compound selected in accordance with this invention can range from 0.5–600 mg.

The pharmaceutical compositions of this invention are preferably packaged in a container (e.g., a box or bottle, or both) with suitable printed material (e.g., a package insert) containing indications, directions for use, etc.

Obviously, numerous modifications and variations of the present invention are possible in light of the above teachings. It is therefore to be understood that within the scope of the appended claims, the invention may be practiced otherwise than as specifically described herein.

We claim:

1. A method of selecting a compound for treatment of a neoplasia to be treated, comprising:
    (a) evaluating the anti-neoplastic activity of the compound against the neoplasia to be treated;
    (b) evaluating whether the compound increases PKG activity in the neoplasia to be treated;
    (c) evaluating whether the compound activates JNK activity in the neoplasia to be treated; and
    (d) selecting the compound that exhibits anti-neoplastic activity, increases PKG activity and activates JNK in the neoplasia to be treated.

2. The method of claim 1 further comprising evaluating whether the compound inhibits PDE5, and selecting the compound that inhibits PDE5.

3. The method of claim 1 further comprising evaluating whether the compound reduces β-catenin in the neoplasia to be treated, and selecting the compound that so reduces β-catenin.

4. The method of claim 1 further comprising evaluating whether the compound inhibits cGMP-specific phosphodiesterase ("PDE") and selecting the compound that inhibits said PDE.

5. The method of claim 1 further comprising evaluating whether the compound increases PKG expression, and selecting the compound if it increases PKG expression.

6. A method for identifying a compound with potential for treating neoplasia, comprising:
    selecting a compound that increases PKG activity and activates JNK in the neoplasia; and
    evaluating the neoplasia growth inhibiting activity of the compound wherein a compound that increases PKG activity, activates JNK and has neoplasia growth inhibiting activity has the potential to inhibit neoplasia without substantially inhibiting the growth of normal cells.

7. A method of selecting a compound for treating neoplasia, comprising
    determining the neoplastic cell growth inhibitory activity of the compound;
    determining whether the compound increases PKG activity and activates JNK in neoplastic cells; and
    selecting the compound that exhibits neoplastic cell growth inhibitory activity, increases PKG activity and activates JNK in neoplastic cells.

8. A method of selecting a compound for treatment of a neoplasia, comprising:
    (a) evaluating whether the compound increases PKG activity in said neoplasia;
    (b) evaluating whether the compound reduces β-catenin in neoplastic cells;
    (c) evaluating whether the compound activates JNK in said neoplasia; and
    (d) selecting the compound that causes an increase PKG activity, activates JNK and causes a decrease in β-catenin in said neoplasia.

* * * * *